United States Patent [19]

Starrett, Jr. et al.

[11] Patent Number: 5,849,923
[45] Date of Patent: Dec. 15, 1998

[54] HETEROCYCLIC-SUBSTITUTED NAPHTHALENYL RETINOBENZOIC ACID DERIVATIVES

[75] Inventors: John E. Starrett, Jr., Middletown, Conn.; David R. Tortolani, Princeton, N.J.; Muzammil M. Mansuri, Lexington, Mass.; Nicholas A. Meanwell, East Hampton, Conn.

[73] Assignee: Bristol-Myers Squibb Company, Princeton, N.J.

[21] Appl. No.: 658,974

[22] Filed: Jun. 4, 1996

Related U.S. Application Data

[62] Division of Ser. No. 417,180, Apr. 5, 1995, Pat. No. 5,559,248.

[51] Int. Cl.[6] ............................................. C07D 213/16
[52] U.S. Cl. .................... 546/340; 546/139; 546/152; 544/336; 544/180; 544/179; 548/146; 548/206; 548/215; 548/240; 548/262.2; 548/255; 548/143; 548/250; 548/127; 548/128; 548/131; 548/136
[58] Field of Search .................... 546/340, 152, 546/139; 544/336, 180, 179; 548/146, 206, 215, 240, 262.2, 255, 143, 250, 127, 128, 136, 131

[56] References Cited

U.S. PATENT DOCUMENTS

| | | | |
|---|---|---|---|
| 3,973,030 | 8/1976 | Bowman et al. | 424/274 |
| 4,510,149 | 4/1985 | Cozzi et al. | 514/341 |
| 4,703,110 | 10/1987 | Shudo | 534/566 |
| 4,777,257 | 10/1988 | Kanao | 546/342 |
| 4,876,349 | 10/1989 | Klaus et al. | 546/350 |
| 5,559,248 | 9/1996 | Starett, Jr. et al. | 549/79 |

FOREIGN PATENT DOCUMENTS

| | | |
|---|---|---|
| 0337689 A1 | 10/1989 | European Pat. Off. |
| WO 84/03505 | 9/1984 | WIPO. |
| WO 93/06086 | 4/1993 | WIPO. |
| WO 93/21146 | 10/1993 | WIPO. |

OTHER PUBLICATIONS

Kagechika et al J. Med. Chem., 1988, vol. 31, pp. 2182–2192.

Hiroyuki Kagechika et al., "Retinobenzoic Acids. I. Structure–Activity Relationships of Aromatic Amides with Retinoidal Activity", *Journal of Medicinal Chemistry*, 31 (11), 2583, 1989.

Peter Loeliger, et al., "Arotinoids, A New Class of Highly Active Retinoids", *Eur. J. Med. Chem., Chimica Therapeutica*, 15, (1) 9–15, Jan.–Feb., 1980.

*Primary Examiner*—Mukund J. Shah
*Assistant Examiner*—Pavanaram K. Sripada
*Attorney, Agent, or Firm*—David M. Morse

[57] ABSTRACT

This invention relates to a compound of formula I

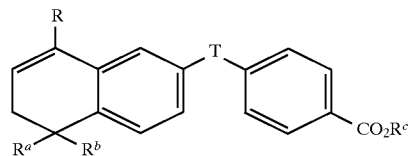

in which
T is —CONH— or —CH=CH—;
$R^a$ and $R^b$ are independently $C_{1-6}$ alkyl;
$R^C$ is $C_{1-6}$ alkyl or hydrogen; and
R is heteroaryl.

13 Claims, 1 Drawing Sheet

HETEROCYCLIC-SUBSTITUTED NAPHTHALENYL RETINOBENZOIC ACID DERIVATIVES

CROSS-REFERENCE TO RELATED APPLICATION(S)

This application is a division of application Ser. No. 08/417,180 filed Apr. 5, 1995, now patented as U.S. Pat. No. 5,559,248.

FIELD OF INVENTION

The present invention provides compounds having retinoid-like activity. More specifically, the compounds of the present invention are useful for preventing and/or treating various skin disorders, such as, but not limited to, acne, psoriasis and damage from irradiation. Further, they have antitumor activities.

BACKGROUND OF THE INVENTION

Retinoic acid and its natural and synthetic analogues (retinoids) exert a wide array of biological effects.

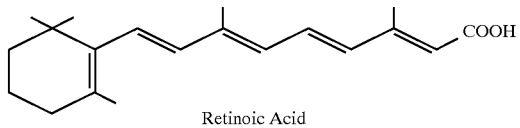

Retinoic Acid

They have been shown to affect cellular growth and differentiation and are promising drugs for the treatment of several cancers. Roberts, A. B. and Sporn, M. B. in "The Retinoids," Sporn, M. B., Roberts, A. B., and Goodman, D. S., eds, 1984, 2, pp. 209–286, Academic Press, New York; Lippman, S. M., Kessler, J. F., and Meyskens, F. L., *Cancer Treat. Rep.*, 1987, 71, p. 391; *ibid., p.* 493; Hong, W. K. et al., *N. Engl. J. Med.*, 1990, 323, p. 795; Huang, M. et al., *Blood,* 1988, 72, p. 567. A few retinoids are already in clinical use in the treatment of dermatological diseases such as acne and psoriasis. For example, isotretinoin is used clinically for oral therapy of severe acne, and etretinate is particularly useful in the treatment of psoriasis. Orfanos, C. E., Ehlert, R., and Gollnick, H., *Drugs,* 1987, 34, pp. 459–503.

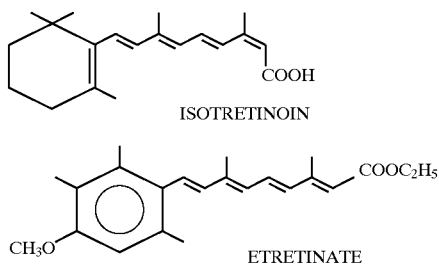

Other examples of retinoid compounds include retinobenzoic acids of formula II and III, in which Q equals —NHCO—, —CONH—, —COCH=CH—, —CH=CHCO—, —COCH$_2$—, etc.

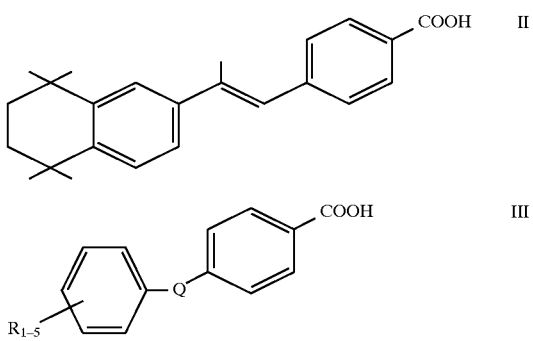

See for example: Loeliger, P., Bollag, W., and Mayer, H., *Eur. J. Med. Chem.* 1980, 15, pp. 9–15; Kagechika, H. et al., *J. Med. Chem.*, 1988, 31, No. 11, pp. 2182–2192.

SUMMARY OF INVENTION

The present invention relates to a compound of formula I

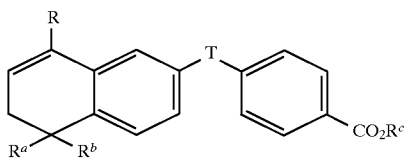

or a nontoxic pharmaceutically acceptable salt, physiologically hydrolyzable ester or solvate thereof, in which T is —CONH— or —CH=CH—;
$R^a$ and $R^b$ are independently $C_{1-6}$ alkyl;
$R^c$ is $C_{1-6}$ alkyl or hydrogen; and
R is a heteroaryl.

Also provided by this invention are methods for preventing and/or treating tumors and non-malignant skin disorders comprising administering a compound of formula I to a mammal. Further provided is a pharmaceutical formulation (composition) comprising a compound of formula I in admixture with (a) pharmaceutically acceptable excipient (s).

DETAILED DESCRIPTION OF THE INVENTION

Figure 1:
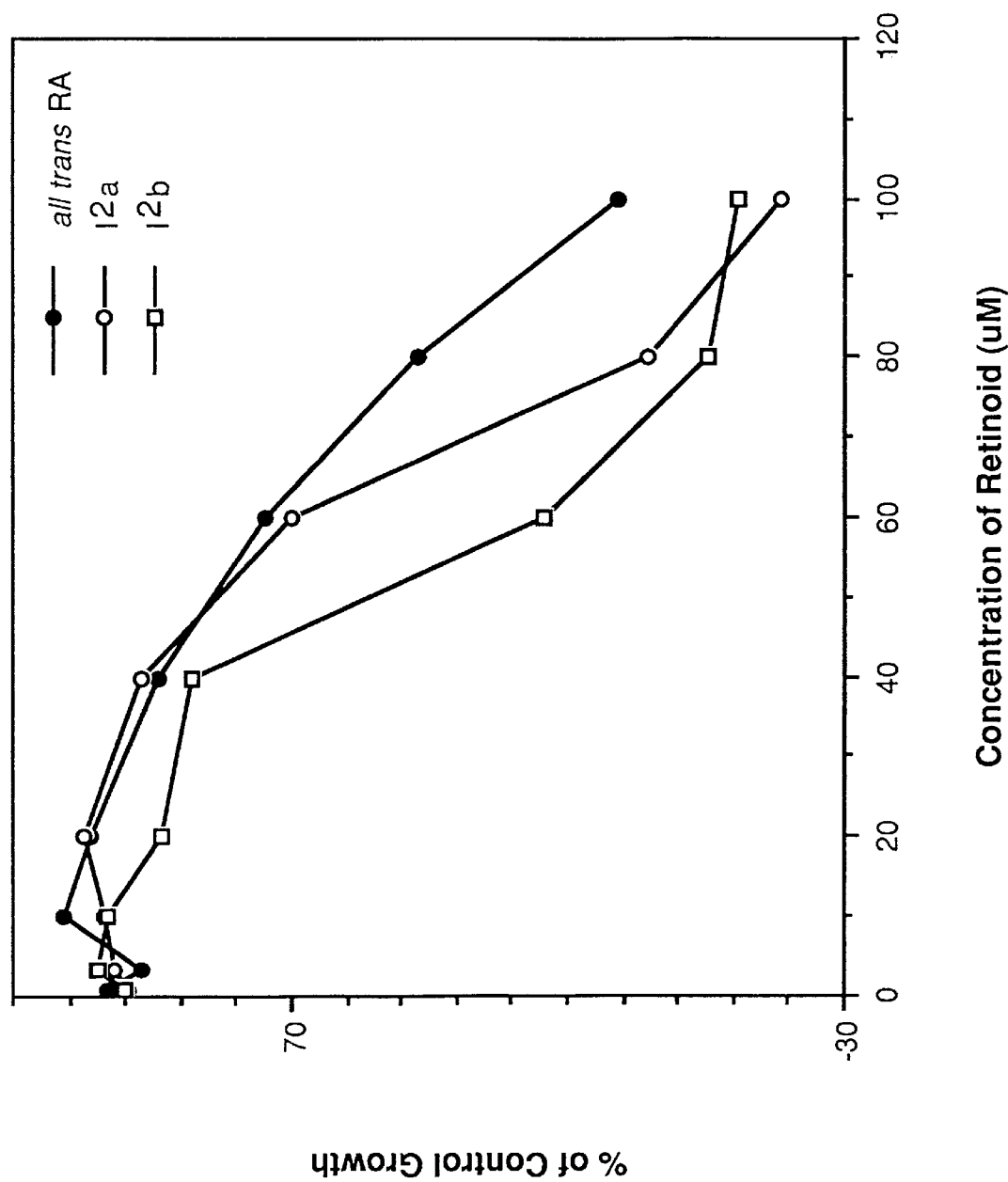
FIG. 1 is the cytotoxicity dose response curves for lung line L2987.

The present invention relates to a compound of formula I

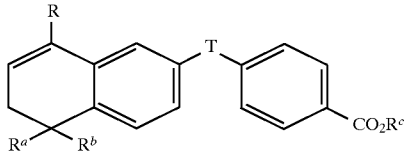

or a nontoxic pharmaceutically acceptable salt, physiologically hydrolyzable ester or solvate thereof, in which T is —CONH— or —CH=CH—;
$R^a$ and $R^b$ are independently $C_{1-6}$ alkyl;
$R^c$ is $C_{1-6}$ alkyl or hydrogen; and
R is heteroaryl.

In the instant application, the numbers in subscript after the symbol "C" define the number of carbon atoms a particular group can contain. For example, $C_{1-6}$alkyl refers to straight and branched chain alkyl groups with one to six carbon atoms and such groups include methyl, ethyl, n-propyl, isopropyl, n-butyl, t-butyl, n-pentyl, n-hexyl, 3-methylpentyl), or the like alkyl groups; $C_{3-6}$cycloalkyl refers to cyclopropyl, cylcobutyl, cyclopentyl, or cyclohexyl; and halogen refers to fluorine, chlorine, bromine, or iodine.

Heteroaryl refers to a fully unsaturated monocylic or bicylic ring structure with 5 or 6 atoms in each ring, and further characterized by having at least one heteroatom, selected from nitrogen, oxygen or sulfur, in at least one ring. For example when heteroaryl is five-membered it contains at least one heteroatom selected from sulfur, oxygen or nitrogen, but up to 1 sulfur, 1 oxygen or 4 nitrogen atoms; when heteroaryl is a six-membered it contains from 1 to 4 nitrogen atoms. Examples of monocylic heteroaryl include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings. Examples of bicyclic heteroaryl include indolyl, isoindolyl, quinolinyl, isoquinolinyl, benzothiazolyl, benzoxazolyl, benzimidazolyl, benzoxadiazolyl, and benzofurazanyl. Heteroaryl can also be optionally substituted with $C_{1-6}$ alkyl. Heteroaryl can also be substituted with one to three $C_{1-6}$ alkyl group(s). Preferred heteroaryl of this invention is a radical of the formula

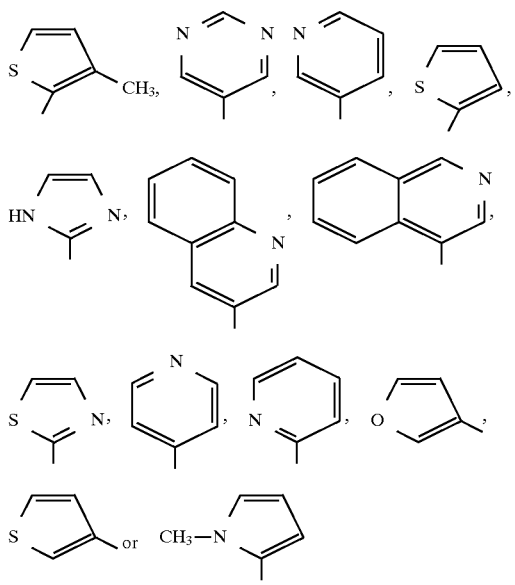

In the instant application all symbols once defined retain the same meaning until they are redefined.

Some compounds of formula I may also form pharmaceutically acceptable metal and amine salts in which the cation does not contribute significantly to the toxicity or biological activity of the salt. These salts are also part of the present invention. Suitable metal salts include the sodium, potassium, calcium, barium, zinc, and aluminum salts. The sodium or potassium salts are preferred. Amines which are capable of forming stable salts group include trialkylamines such as triethylamine, procaine, dibenzylamine, N-benzyl-β-phenethylamine, 1-ephenamine, N,N-'-dibenzylethylenediamine, dehydroabietylamine, N-ethylpiperidine, benzylamine, dicyclohexylamine, or the like pharmaceutically acceptable amines.

When compounds of formula I contains carboxy groups, it can form physiologically hydrolyzable esters which serve as prodrugs by being hydrolyzed in the body to yield formula I compounds per se. They are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, benzyl, 4-methoxybenzyl, indanyl, phthalidyl, methoxymethyl, $C_{1-6}$alkanoyloxyl$C_{1-6}$alkyl, e.g. acetoxymethyl, pivaloyloxymethyl or propionyloxymethyl, $C_{1-6}$alkoxycarbonyloxy$C_{1-6}$alkyl, e.g. methoxycarbonyloxymethyl or ethoxycarbonyloxymethyl, glycyloxymethyl, phenylglycyloxymethyl, (5-methyl-2-oxo-1-3-dioxolen-4-yl)-methyl and other well-known physiologically hydrolyzable esters used, for example, in the penicillin and cephalosporin arts. Such esters are prepared by conventional techniques known in the art.

The structural formulae as drawn in the instant application are believed to best represent the structures of compounds of the present invention. However, some compounds within the scope of the invention may exist as other tautomeric forms, in which hydrogen atoms are transposed to other parts of the molecules and the chemical bonds between the atoms of the molecules are consequently rearranged. It should be understood that the structural formulae represent all tautomeric forms, insofar as they may exist.

The synthesis of a compound of formula I can be accomplished by a wide variety of methods using conventional starting materials and processes. The synthetic descriptions and specific examples that follow are only intended for the purpose of illustration, and are not to be construed as limiting in any manner ways to make compounds of the present invention by any other methods.

Typically a compound of formula I may be made by employing one of the processes as depicted in Schemes I to VI or obvious variations thereof. All the steps in Schemes I to VI are standard processes which can be easily practiced by anyone skilled in the art. The specific examples that follow are intended to illustrate specific conditions which may be employed to carry certain steps in the Schemes and are not to be construed as limiting the conditions in any way.

In the Schemes, $R^1$ is a carboxy protecting group preferably $C_{1-6}$alkyl; and even more preferably it is methyl, ethyl or t-butyl. When $R^1$ is t-butyl, it can be removed by trifluoroacetic acid. In Scheme IV, $R^d$ refers to an amide protecting group as represented by t-butoxycarbonyl or 2-(trimethylsilyl)ethoxymethyl.

Scheme I

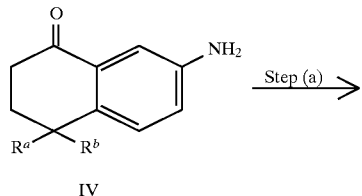

IV

5
-continued
Scheme I
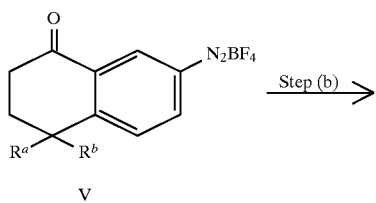
V
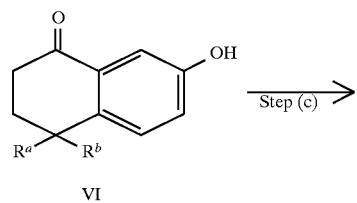
VI
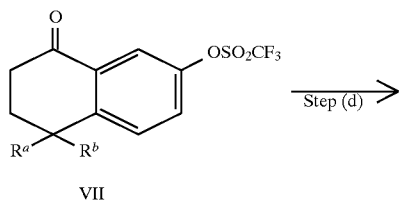
VII
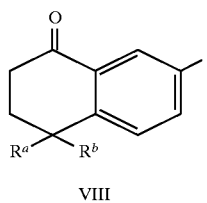
VIII
Scheme II
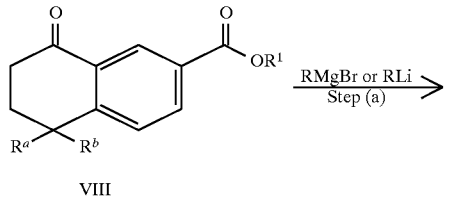
VIII
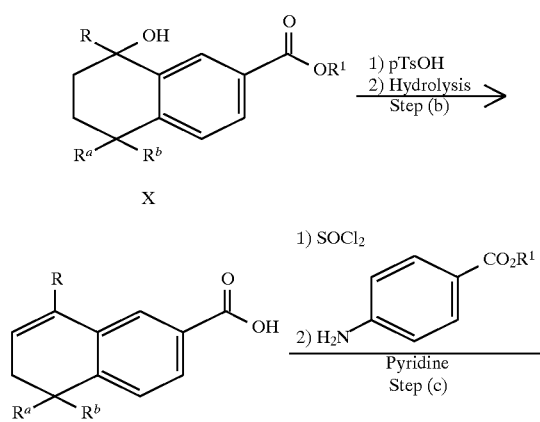
X
XI
6
-continued
Scheme II
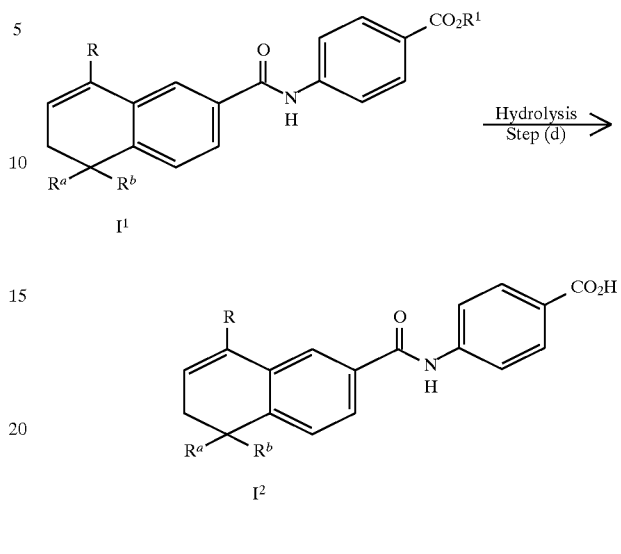
I¹
I²
Scheme III
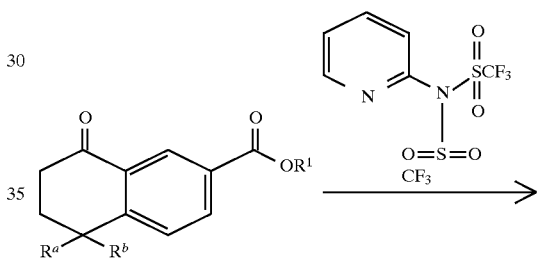
VIII
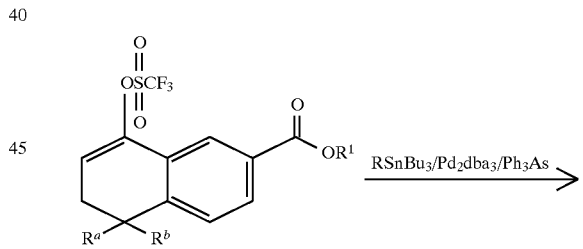
XII
XIII -continued
Scheme III
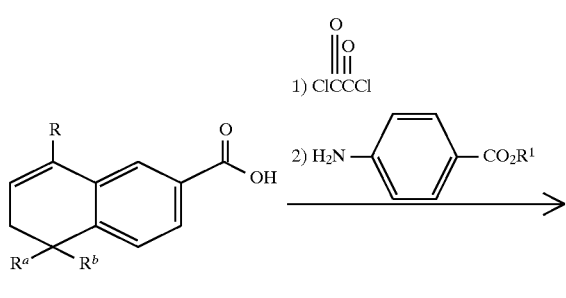
XI
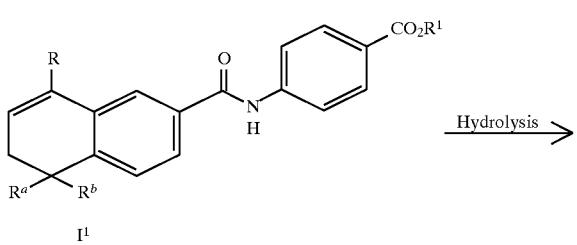
I¹
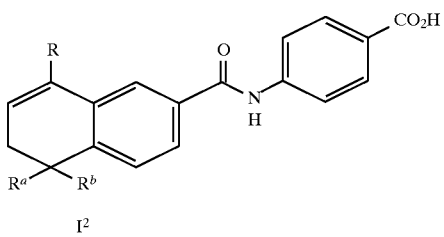
I²
Scheme IV
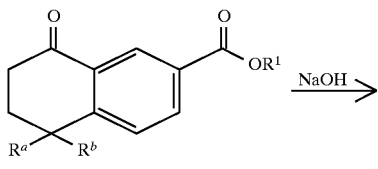
VIII
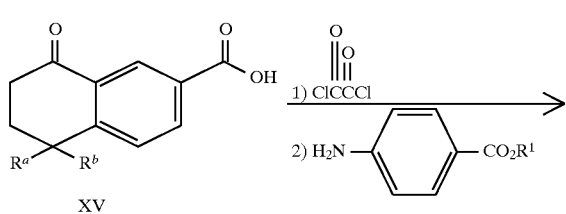
XV
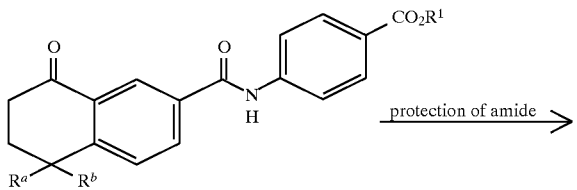
XVI
-continued
Scheme IV
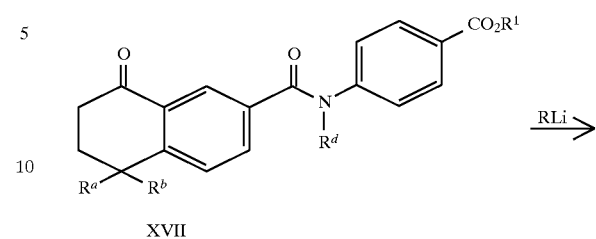
XVII
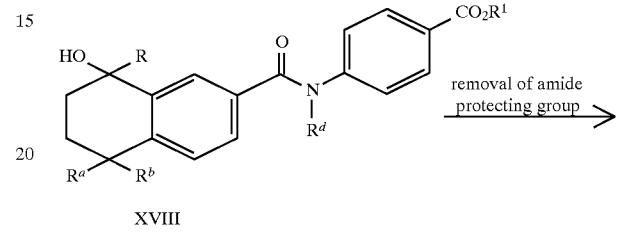
XVIII
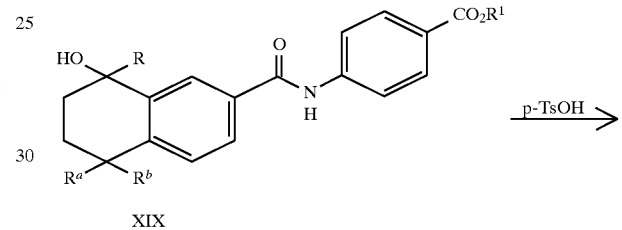
XIX
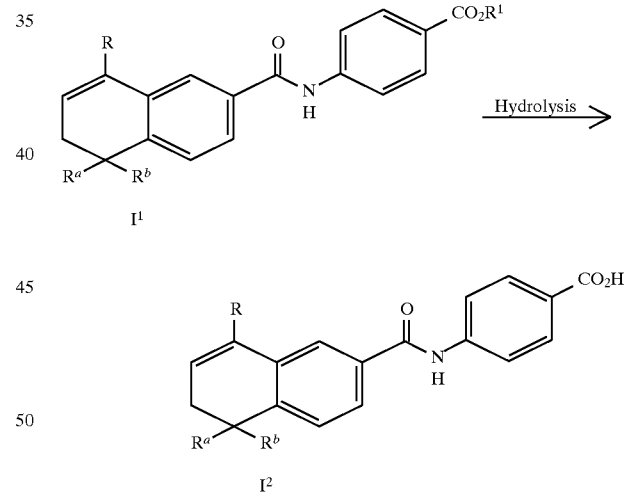
I¹
I²

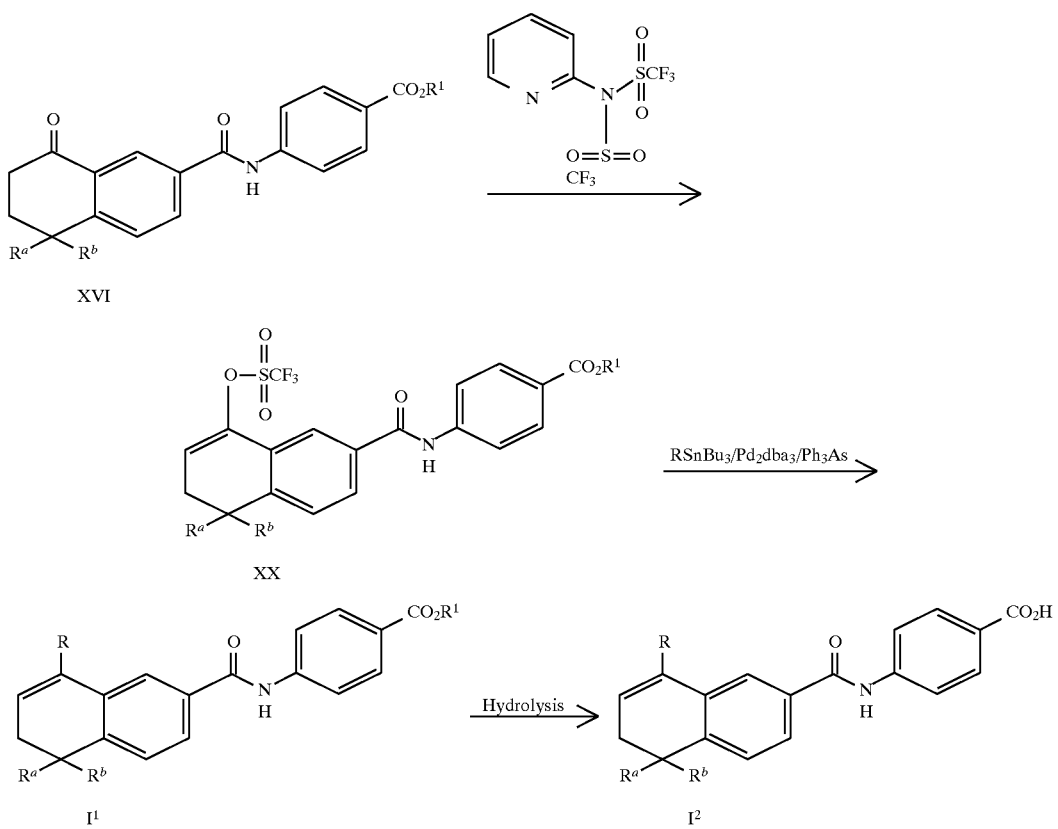
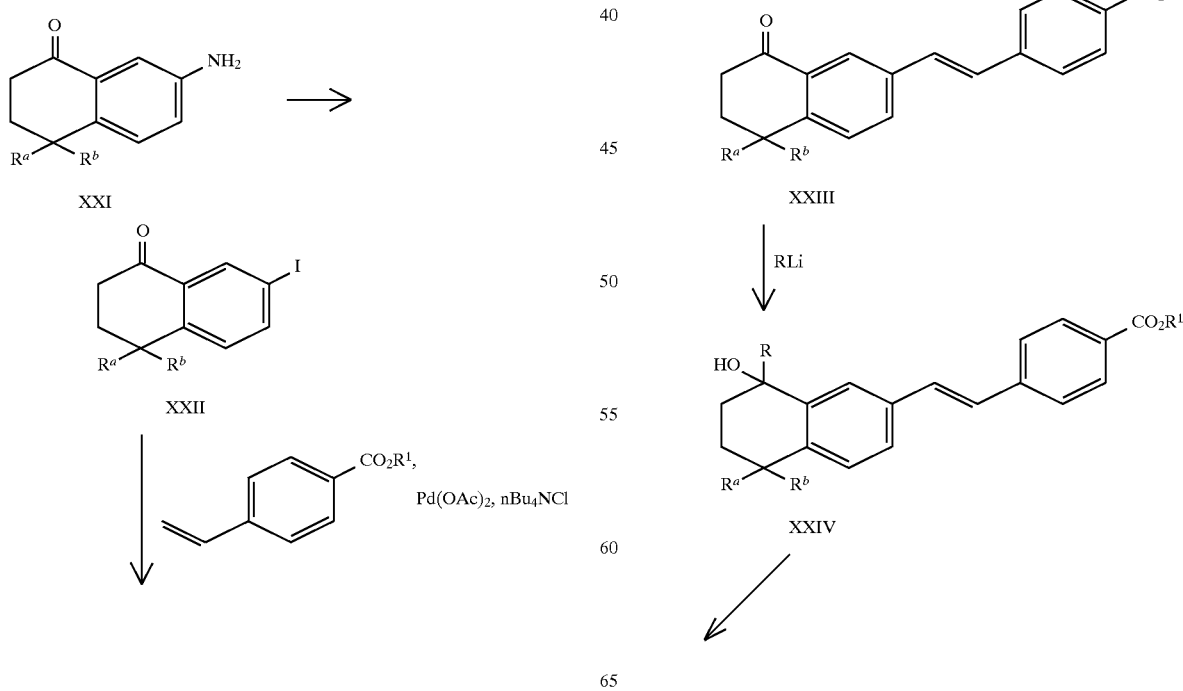

-continued
SCHEME VI

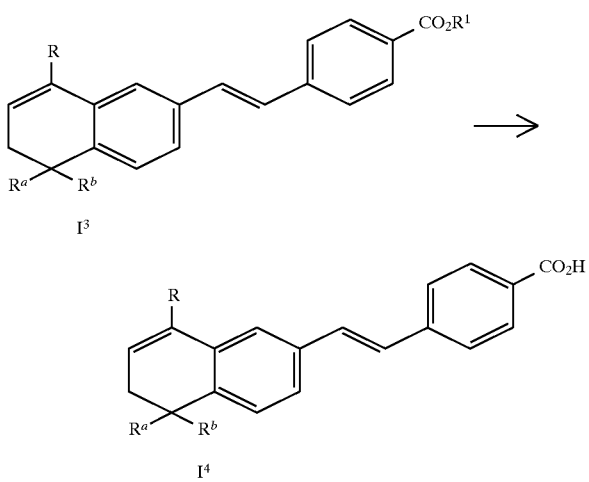

DESCRIPTION OF SPECIFIC EMBODIMENTS

The specific examples which follow illustrate the synthesis of representative compounds of the instant invention and are not to be construed as limiting the invention in sphere or scope. The methods may be adapted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiplet (m), doublet (d), quartet (q), triplet (t), doublet of doublet (dd), doublet of triplet (dt), and doublet of quartet (dq). The solvents employed for taking NMR spectra are DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value.

Celite is a registered trademark of the Johns-Manville Products Corporation for diatomaceous earth.

The abbreviations used herein are conventional abbreviations widely employed in the art. Some of which are:

MS:mass spectrometry
HRMS:high resolution mass spectrometry
Ar:aryl
DCI:desorption chemical ionization
Hex:hexane(s)
tBu:tertiarybutyl
h:hour(s)
min:minute(s)
Ph:phenyl
Y:yield
THF:tetrahydrofuran $Tf_2O$:triflic anhydride (trifluoromethanesulfonic anhydride)
$Pd_2dba_3$:tris(dibenzylidene acetone)-dipalladium (0)
SEMC1:2-(trimethylsilyl)ethoxymethyl chloride
IS:Ion spray

EXAMPLE 1

4,4-Dimethyl-7-diazotetrafluoroborate-1-tetralone (Va)

To 4,4-dimethyl-7-amino-1-tetralone (15.10 g, 79.89 mmol) was added 48% fluoroboric acid (28 mL) diluted with water (28 mL) at 0° C. A cold solution of sodium nitrate (13.75 g, 199 mmol) in water (28 mL) was added slowly while keeping the temperature at about 10° C. The mixture was then cooled to 0° C., filtered and washed with 5% fluoboric acid (200 mL) and dried in vacuo to give 20.5 g (Y: 89%) of the title compound. $^1$H-NMR (DMSO-$d_6$): $\delta$9.15 (d, J=2.5 Hz, 1H), 8.75 (dd, J=8.5, 2.5 Hz, 1H), 8.20 (d, J=8.5 Hz, 1H), 2.87 (t, J=7.0 Hz, 2H), 2.07 (t, J=7.0 Hz, 2H), 1.43 (s, 6H); MS (DCI) m/e: 193 ($MH^+$—$N_2BF_4$).

EXAMPLE 2

4,4-Dimethyl-7-hydroxy-1-tetralone (VIa)

Compound Va (1.19g, 4.13 mmol) was added to an already boiling solution of sulfuric acid (3 mL) and water (30 mL). After 1 hour at reflux the reaction mixture was cooled and extracted with ethyl acetate (2×50 mL). The combined organic phases were concentrated in vacuo and the residue chromatographed on silica gel (eluted with 20% ethyl acetate in hexane) to give 690 mg (Y: 88%) of the title compound. $^1$H-NMR ($CDCl_3$) $\delta$7.48 (d, J=2.5 Hz, 1H), 7.33 (d, J=8.5 Hz, 1H), 7.05 (dd, J=8.5, 2.5 Hz, 1H), 2.75 (t,J=7.0 Hz, 2H), 2.00 (t, J=7.0 Hz, 2H), 1.38 (s, 6H).

EXAMPLE 3

4,4-Dimethyl-7-trifluoromethanesulfonate-1-tetralone (VIIa)

To a solution of compound VIa (690 mg, 3.63 mmol) in anhydrous pyridine (10 mL) was added trifluoromethanesulfonic anhydride (4.42 mmol, 0.74 mL) at 0° C. The reaction mixture was then allowed to warm to room temperature. After 16 hours, 1N HCl (25 mL) was added and the mixture was extracted with ethyl acetate (2×50 mL). The combined organic phases were dried over anhydrous magnesium sulfate and concentrated in vacuo to give 1.17 g (Y: 100%) of the title compound. $^1$H-NMR ($CDCl_3$): $\delta$7.88 (d, J=2.8 Hz, 1H), 7.52 (d, J=8.7 Hz, 1H), 7.40 (dd, J=8.7, 2.8 Hz, 1H), 2.76 (t, J=7.0 Hz, 2H), 2.04 (t, J=7.0 Hz, 2H), 1.40 (s, 6H); MS (DCI) m/e: 323 ($MH^+$).

EXAMPLE 4

5,5-Dimethyl-8-oxo-5,6,7,8-tetrahydronaphthalene-2-carboxylic acid, methyl ester (VIIIa)

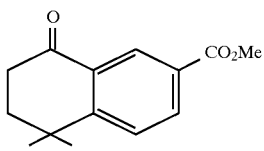

To a solution of compound VIIa (1.15 g, 3.57 mmol) in methanol (11 mL) and dimethyl sulfoxide (11 mL) was added triethylamine (1.09 mL, 7.82 mmol) palladium (II) acetate (24 mg, 0.11 mmol) and 1,3-bis(diphenylphosphino)

propane (44 mg, 0.11 mmol). The reaction mixture was then saturated with carbon monoxide at room temperature and heated to 70° C. under a balloon of carbon monoxide for 3 hours. After cooling to room temperature, the reaction mixture was poured into water and extracted with ethyl acetate. The organic phase was then concentrated in vacuo and the residue chromatographed on silica gel (eluted with 15% ethyl acetate in hexane) to give 692 mg (Y: 93%) of the title product. $^1$H-NMR (CDCl$_3$): δ8.66 (d, J=2.0 Hz, 1H), 8.18 (dd, J=8.3, 2.0 Hz, $^1$H), 7.52 (d, J=8.3 Hz, 1H), 3.92 (s, 3H), 2.76 (t, J=7.0 Hz, 2H), 2.04 (t, J=7.0 Hz, 2H), 1.41 (s, 6H); MS (DCI) me: 233 (MH$^+$).

EXAMPLE 5

5,5-Dimethyl-8-hydroxy-8-(2-thienyl)-5,6,7,8-tetrahydro-naphthalene-2-carboxylic acid, methyl ester (Xa)

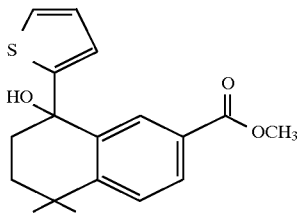

To a solution of compound VIIIa (275 mg, 1.19 mmol) in tetrahydrofuran (5 mL) at −78° C. was added 2-thienyllithium (1.0M solution in tetrahydrofuran, 1.78 mmol, 1.78 mL). After warming to room temperature (2 hours), the reaction mixture was concentrated and the residue chromatographed on silica gel (eluted with 10% ethyl acetate in hexane) to give 252 mg (Y: 67%) of the title product. Title product upon isolation, was not stable and some elimination occurred. Mixture was used as is in the following step:

EXAMPLE 6

5,5-Dimethyl-5,6-dihydro-8-(2-thienyl)-naphthalene-2-carboxylic acid (XIa)

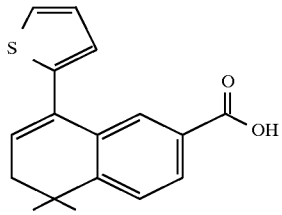

To a solution of compound Xa (252 mg, 0.80 mmol) in toluene (10 mL) was added (3–6 mg) of p-toluenesulfonic acid. After heating at 70° C. for 5 minutes, the reaction mixture was cooled and concentrated in vacuo. The residue was then dissolved in ethyl alcohol (7 mL) and treated with 10N NaOH (10.0 mmol, 1.0 mL) at room temperature. After 16 h an excess of 1N HCl (30 mL) was added and the precipitate collected by vacuum filtration to give 195 mg (Y: 86%) of the title product. $^1$H NMR (DMSO): δ7.86 (m, 2H), 7.55 (d, J=4.0 Hz, 1H), 7.50 (d, J=8.0 Hz, 1H), 7.13 (m, 2H), 6.23 (t, J=4.5 Hz, 1H), 2.33 (d, J=4.5 Hz, 2H), 2.33 (s, 6H). MS (DCI) m/e: 285 (MH$^+$).

EXAMPLE 7

4-[[[[5,6-Dihydro-5,5-dimethyl-8-(2-thienyl)]-2-naphthalenyl]carbonyl]amino]benzoic acid, methyl ester (I$^a$)

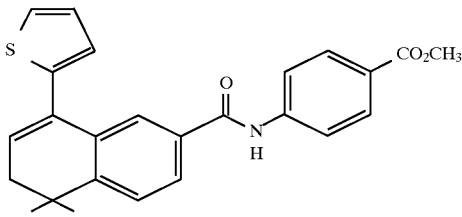

A solution of compound XIa (195 mg, 0.69 mmol) in anhydrous methylene chloride (7 mL) was treated with oxalyl chloride (0.20 mL, 2.29 mmol) and 2 drops of N,N-dimethylformamide at 0° C. The reaction mixture was then allowed to stir at room temperature. After 2 hours, the mixture was concentrated in vacuo. The residue was dissolved in anhydrous pyridine (6 mL) to which was added methyl 4-aminobenzoate (Aldrich, 104 mg, 0.69 mmol). After 2 hours at room temperature, the mixture was diluted with 1N HCl, extracted with ethyl acetate (100 mL), washed with 1N HCl (3×100 mL) and washed with saturated sodium bicarbonate (2×100 mL). The organic phase was then separated, concentrated in vacuo and the residue chromatographed on silica gel (eluted with 20% ethyl acetate in hexane) to give 166 mg (Y: 58%) of the title product. $^1$H NMR (CDCl$_3$): δ8.05 (d, J=8.7 Hz, 1H), 7.88 (d, J=1.9 z, 1H), 7.80–7.65 (m, 6H), 7.50 (d, J=8.0 Hz, 1H), 7.10 (d, J=2.9 Hz, 1H), 6.27 (t, J=4.5 Hz, 1H), 3.91 (s, 3H), 2.38 (d, J=4.5 Hz, 2H), 1.36 (s, 6H). MS (DCI) m/e: 418 (MH+)

EXAMPLE 8

4-[[[[5,6-Dihydro-5,5-dimethyl-8-(2-thienyl)]-2naphthalenyl]carbonyl]amino]benzoic acid (I$^2$a)

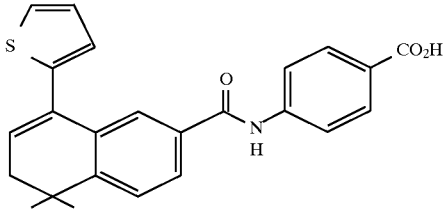

To a stirred solution of compound I$^1$a (166 mg, 0.45 mmol) in absolute ethyl alcohol (7 mL) was added 10N NaOH (0.40 mL, 4.0 mmol) at room temperature. After 24 hours, an excess of 1N HCl (30 mL) was added. The precipitate was collected by vacuum filtration, washed with 1N HCl and air dried to give 131 mg (Y: 82%) of the title compound. $^1$H NMR (DMSO): δ12.76 (s, 1H), 10.49 (s, 1H), 7.90 (m, 6H), 7.53 (m, 2H), 7.14 (m, 2H), 6.26 (t, J=4.5 Hz, 1H), 2.34 (d, J=4.5 Hz, 2H), 1.29 (s, 6H). $^{13}$C NMR: 166.94, 165.99, 148.65, 143.29, 141.30, 132.66, 132.57, 131.37, 130.23, 128.70, 127.64, 127.29, 125.94, 125.41, 125.14, 124.78, 124.12, 119.42, 37.79, 33.42, 27.67. MS (DCI) m/e: 404 (MH$^+$).IR (KBr): 2960, 1688, 1594, 1520. Anal. calcd for C$_{24}$H$_{21}$O$_3$N$_1$S$_1$·0.25 H$_2$O: C, 70.65; H, 5.31; N, 3.43. Found: C, 70.40; H 5.24; N, 3.21.

EXAMPLE 9

5,5-Dimethyl-8-hydroxy-8-[2-(3-methylthienyl)]-5,6,7,8-tetrahydro-naphthalene-2-carboxylic acid, methyl ester (Xb)

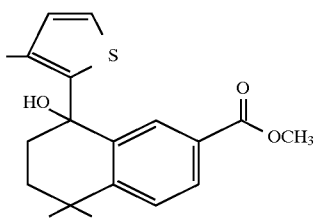

To a solution of compound VIIIa (200 mg, 0.86 mmol) in tetrahydrofuran (4 mL) at −50° C. was added 3-methyl-2-thienyllithium [0.25M solution in THF, 1.29 mmol, 5.17 mL; prepared by treating 3-methyl-2-bromothiophene (909 mg, 5.13 mmol) in tetrahydrofuran (18.4 mL) with n-butyllithium (2.5N solution in hexanes, 5.375 mmol, 2.15 mL) at −78° C. After 5 minutes at −78° C., 5.17 mL was transferred via syringe to the solution of compound VIIIa. After warming to room temperature, the reaction mixture was concentrated and the residue chromotographed on silica gel (eluted with 10% ethyl acetate in hexane) to give 70 mg (Y: 25%) of the title compound. $^1$H NMR (CDCl$_3$): δ7.95 (m, 2H), 7.47 (d, J=9.0 Hz, 1H), 7.10 (d, J=5.0 Hz, 1H), 6.80 (d, J=5.0 Hz, 1H), 3.85 (s, 3H), 2.40 (m, 1H), 2.10 (m, 2H), 1.82 (s, 3H), 1.65 (m, 1H), 1.45 (s, 3H), 1.35 (s, 3H). MS (DCI) m/e: 331 (MH$^+$).

EXAMPLE 10

5,5-Dimethyl-5,6-dihydro-8-[2-(3-methylthienyl)]naphthalene-2-carboxylic acid (XIb)

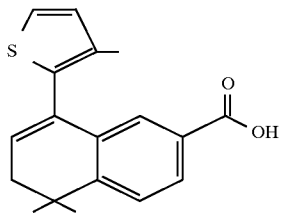

Using the method given for the preparation of the 8-(2-thienyl) derivative XIa, 240 mg (0.73 mmol) of compound Xb gave 209 mg (Y: 92%) of the title product. $^1$H NMR (CDCl$_3$): δ7.93 (d, J=8.0 Hz, 1H), 7.64 (s, 1H), 7.42 (d, J=8.0 Hz, 1H), 7.19 (d, J=5.0 Hz, 1H), 6.90 (d, J=5.3 Hz, 1H), 6.13 (t, J=4.5 Hz, 1H), 2.39 (d, J=4.5 Hz, 2H), 2.01 (s, 3H), 1.36 (s, 6H). MS (DCI) me: 299 (MH$^+$)

EXAMPLE 11

4-[[[[5,6-Dihydro-5,5-dimethyl-8-[2-(3-methylthienyl)]]-2-naphthalenyl]carbonyl]amino]benzoic acid methyl ester (I$^1$b)

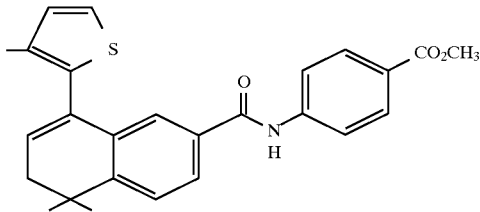

Using the method given for the preparation of the 8-(2-thienyl) derivative I$^1$a, 195 mg (0.65 mmol) of compound XIb gave 220 mg (Y: 78%) of the title product. $^1$H NMR (CDCl$_3$): δ8.03 (d, J=8.7 Hz, 2H), 7.70 (s, 1H), 7.71 (d, J=2.0 Hz, 1H), 7.67 (d, J=8.7 Hz, 2H), 7.48 (d, J=8.0 Hz, 1H), 7.43 (d, J=2.0 Hz, 1H), 7.22 (d, J=5.0 Hz, 1H), 6.92 (d, J=5.0 Hz, 1H), 6.17 (t, J=4.5 Hz, 1H), 3.91 (s, 3H), 2.41 (d, J=4.5 Hz, 2H), 2.05 (s, 3H), 1.38 (s, 6H). MS (DCI) m/e: 432 (MH$^+$).

EXAMPLE 12

4-[[[[5,6-Dihydro-5,5-dimethyl-8-2-(3-methylthienvl)]]-2-naphthalenyl]carbonyl]amino]benzoic acid (I$^2$b)

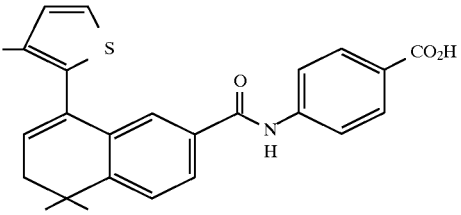

Using the method given for the preparation of the 8-(2-thienyl) derivative I$^1$a, 220 mg (0.74 mmol) of compound I$^1$b gave 50 mg (Y: 24%) of the title product. $^1$H NMR (DMSO): δ12.73 (s, 1H), 10.45 (s, 1H), 7.87 (m, 5H), 7.53 (d, J=8.0 Hz, 1H), 7.45 (d, J=5.0 Hz, 1H), 7.35 (d, J=1.9 Hz, 1H), 6.98 (d, J=5.0 Hz, 1H), 6.15 (t, J=4.5 Hz, 1H), 2.38 (d, J=4.5 Hz, 2H), 1.96 (s, 3H), 1.33 (s, 6H). MS (DCI) m/e: 418 (MH$^+$). HRMS Deviation 2.2 ppM. Calc. 418.1477. Found: 418.1468. IR (KBr): 2960, 1688, 1594, 1520.

EXAMPLE 13

5,5-Dimethyl-8-hvdroxy-8-(5-pyrimidinyl)-5,6,7,8-tetrahydro-naphthalene-2-carboxylic acid, methyl ester (Xc)

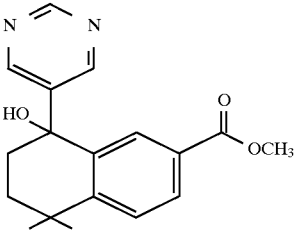

Using the method given for the preparation of the 8-[2-(3-methylthienyl)] derivative Xb, reaction at −78° C. of compound VIIIa (535 mg, 2.31 mmol) and 5-pyrimidinyl lithium (0.29M solution in THF, 2.88 mmol, 10.0 ml; prepared by treating 5-bromopyrimidine in THF with n-butyllithium at −78° C.) gave 84 mg (Y: 12%) of the title compound. Title product upon isolation was not stable and some elimination occurred. Mixture was used as is in the following step.

EXAMPLE 14

5,5-Dimethyl-5,6-dihydro-8-(5-pyrimidinyl)-naphthalene-2-carboxylic acid (XIc)

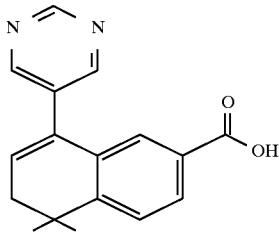

Using the method given for the preparation of the 8-(2-thienyl) derivative XIa, 167 mg (0.535 mmol) of compound Xc gave 140 mg (Y: 93%) of the title product. $^1$H NMR (DMSO): δ9.23 (s, 1H), 8.82 (s, 2H), 7.87 (dd, J=8.0, 1.7 Hz, 1H), 7.56 (d, J=8.0 Hz, 1H), 7.38 (d, J=1.6 Hz, 1H), 6.28 (t, J=4.5 Hz, 1H), 2.41 (d, J=4.5 Hz, 2H), 1.32 (s, 6H). MS (DCI) m/e: 281 (MH$^+$)

EXAMPLE 15

4-[[[[5,6-Dihydro-5,5-dimethyl-8-(5-pyrimidinyl)1-2-naphthalenyl]carbonyl]amino]benzoic acid, methyl ester (I$^1$c)

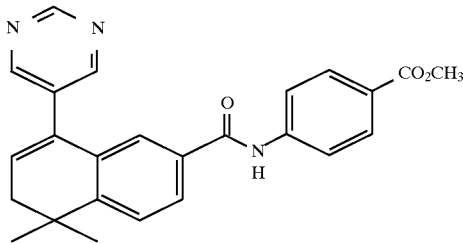

Using the method given for the preparation of the 8-(2-thienyl) derivative I$^1$a, 140 mg (0.50 mmol) of compound XIc gave 60 mg (Y: 29%) of the title product. $^1$H NMR (CDCl$_3$): δ8.17 (d, J=8.6 Hz, 1H), 8.03 (d, J=8.4 Hz, 2H), 7.76 (d, J=8.5 Hz, 1H), 7.67 (m, 3H), 7.54 (d, J=8.0 Hz, 1H), 7.40 (s, 1H), 6.19 (t, J=4.5 Hz, 1H), 3.90 (s, 3H), 2.47 (d, J=4.5 Hz, 2H), 1.39 (s, 6H). MS (DCI) m/e: 414 (MH$^+$).

EXAMPLE 16

4-[[[[5,6-Dihydro-5,5-dimethyl-8-(5-pyrimidinyl)]-2-naphthalenyl]carbonyl]amino]benzoic acid (I$^2$c)

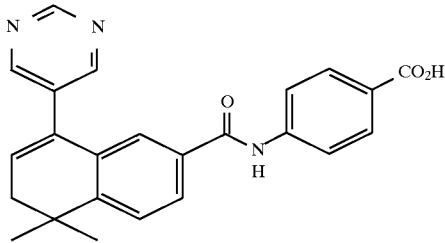

Using the method given for the preparation of the 8-(2-thienyl) derivative I$^2$a, 60 mg (0.15 mmol) of compound I$^1$c gave 16 mg (Y: 28%) of the title product. $^1$H NMR (DMSO): δ10.45 (s, 1H), 9.22 (s, 1H), 8.84 (s, 2H), 7.93–7.80 (m, 5H), 7.59 (d, J=8.1 Hz, 1H), 7.39 (d, J=1.7 Hz, 1H), 6.30 (t, J=4.5 Hz, 1H), 2.42 (d, J=4.5 Hz, 2H), 1.34 (s, 6H). MS (DCI) m/e: 400 (MH$^+$). HRMS Deviation 3.1 ppM. Calcd: 400.1661. Found: 400.1649. IR (KBr): 2960, 1684, 1596, 1526.

EXAMPLE 17

N-(2-Pyridyl)triflimide

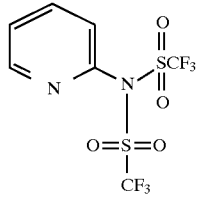

The title compound was prepared by procedure of Comins & Dehghani, *Tetrahedron Lett.*, Vol. 33, No. 42, 1992, p. 6299. $^1$H NMR (CDCl$_3$): δ8.66 (m, 1H), 7.95 (m, 1H), 7.56 (m, 1H), 7.48 (d, 1H). MS (DCI) m/e: 359 (MH$^+$).

EXAMPLE 18

5,5-Dimethyl-5,6-dihydro-8-(trifluoromethanesulfonyloxy)-naphthalene-2-carboxylic acid, methyl ester (XIIa)

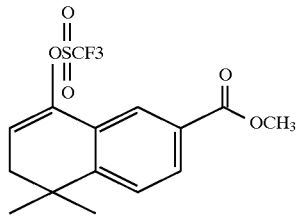

To a solution of compound VIIIa (606 mg, 2.61 mmol) in tetrahydrofuran (15 mL) at −78° C. was added lithium bis(trimethylsilyl) amide (1.0M solution in hexane, 2.87 mmol, 2.87 mL) and then N-(2-pyridyl) triflimide (2.87 mmol, 1.03 g) at −78° C. Reaction mixture was stirred at −78° C. for 0.5 h and then warmed to room temperature. The mixture was diluted with water and extracted with ethyl acetate (2 ×50 mL). The organic phases were combined and concentrated in vacuo. The residue was chromatographed on silica gel (eluted with 5% ethyl acetate in hexane) to give 844 mg (Y: 89%) of the title product. $^1$H NMR (CDCl$_3$): δ8.05 (m, 2H), 7.40 (d, J=8.0 Hz, 1H), 6.05 (t, J=4.5 Hz, 1H), 3.92 (s, 3H), 2.46 (d, 4.5 Hz, 2H), 1.33 (s, 6H).

EXAMPLE 19

3-Tributylstannylfuran

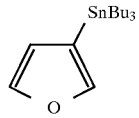

A solution of 3-bromofuran (Aldrich, 300 g, 20.4 mmol) in anhydrous toluene (50 mL) was treated with bis (tributyltin) (Aldrich, 27.8g, 47.9 mmol) and tetrakis (triphenylphosphine)palladium (0) (Aldrich, 0.20 mmol, 236 mg). The reaction mixture was allowed to reflux for 16 hours. The mixture was then concentrated in vacuo and the residue was chromatographed on C-18 (eluted with 100% methylene chloride) to give 3.31 g (Y: 50%) of the title product. $^1$H NMR (CDCl$_3$): δ7.57 (s, 1H), 7.25 (d, J=6.0 Hz, 1H), 6.36 (s, 1H), 1.52 (m, 6H), 1.31 (m, 6H), 1.00 (t, J=8.2 Hz, 6H), 0.92 (t, J=7.4 Hz, 9H). MS (DCI) m/e: 359 (MH$^+$).

EXAMPLE 20

5,5-Dimethyl-5,6-dihydro-8-(3-furyl)-naphthalene-2-carboxylic acid, methyl ester (XIIIa)

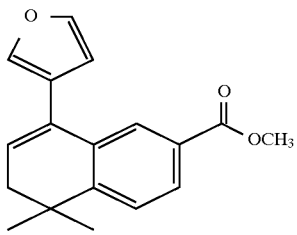

A solution of compound XIIa (309 mg, 0.85 mmol) in anhydrous 1-methyl-2-pyrrolidinone (4 mL) was treated with triphenylarsine (49 mg, 0.16 mmol) and tris(dibenzylidene acetone)-dipalladium (0) (24 mg, 0.026 mmol) at room temperature. After 5 minutes, 3-tributylstannylfuran (610 mg, 1.87 mmol) in anhydrous 1-methyl-2-pyrrolidinone (1 mL) was added to the reaction mixture. After 1 hour at room temperature, the mixture was diluted with water and extracted with ethyl acetate (2×50 mL). The organic phases were combined and concentrated in vacuo. The residue was chromatographed on silica gel (eluted with 10% ethyl acetate in hexane) to give 240 mg (Y: 99%) of the title product. $^1$H NMR (CDCl$_3$): d 7.97 (s, 1H), 7.91 (dd, J=8.0, 1.8 Hz, 1H), 7.54 (s, 1H), 7.49 (d, J=1.8 Hz, 1H), 7.42 (d, J=8.0 Hz, 1H), 6.50 (s, 1H), 6.10 (t, J=4.5 Hz, 1H), 3.87 (s, 3H), 2.32 (d, J=4.5 Hz, 2H), 1.33 (s, 6H). MS (DCI) m/e: 283 (MH$^+$).

EXAMPLE 21

5,5-Dimethyl-5,6-dihydro-8-(3-furyl)-naphthalene-2-carboxylic acid (XId)

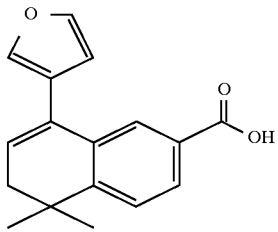

To a stirred solution of compound XIIIa (0.75 mmol, 210 mg) in ethanol (5 mL) was added 10N NaOH (0.75 mL, 7.5 mmol) at room temperature. After 3 hours, an excess of 1N HCl (30 mL) was added. The precipitate was collected by vacuum filtration, washed with 1N HCl and air dried to give 175 mg (Y: 88%) of the title compound. $^1$H NMR (DMSO): δ7.84 (s, 1H), 7.81 (s, 2H), 7.76 (d, J=1,5 Hz, 1H), 7.49 (d, J=7.8 Hz, 1H), 6.61 (s, 1H), 6.15 (t, J=4.5 Hz, 1H), 2.30 (d,J=4.5 Hz, 2H), 1.27 (s, 6H). MS (DCI) m/e 269 (MH$^+$).

EXAMPLE 22

4-[[[[5,6-Dihydro-5,5-dimethyl-8-(3-furyl)1-2-naphthalenyl]carbonyl]amino]benzoic acid, methyl ester (IIId)

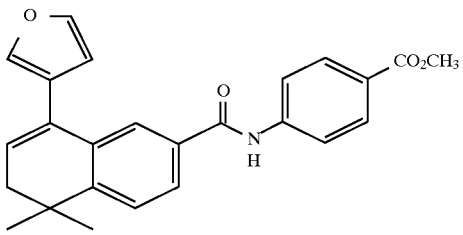

Using the method given for the preparation of the 8-(2-thienyl) derivative IIa, 175 mg (0.653 mmol) of compound XId gave 140 mg (Y:53%) of the title product. $^1$H NMR (CDCl$_3$): δ8.05 (d, J=8.7 Hz, 2H), 7.75 (m, 4H), 7.56 (s, 1H), 7.49 (d, J=8.3 Hz, 2H), 6.51 (s, 1H), 6.15 (t, J=4.5 Hz, 1H), 3.91, (s, 3H), 2.35 (t, J =4.5 Hz, 2H), 1.35 (s, 6H). MS (DCI) m/e: 402 (MH$^+$)

EXAMPLE 23

4-[[[[5,6-Dihydro-5,5-dimethyl-8-(3-furyl)]-2-naphthalenyl]carbonyl]amino]benzoic acid (I$^2$d)

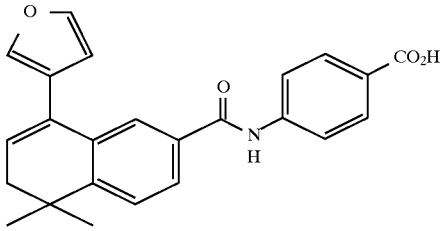

Using the method given for the preparation of the 8-(2-thienyl) derivative I$^2$a, 140 mg (0.35 mmol) of compound I$^1$d gave 114 mg (Y: 84%) of the title product. $^1$H NMR (DMSO): δ12.76 (s, 1H), 10.48 (s, 1H), 7.95–7.75 (m, 8H), 7.52 (d, J=8.0 Hz, 1H), 6.66 (d, J=1.8 Hz, 1H), 6.18 (t, J=4.5 Hz, 1H), 2.29 (d, J=4.5 Hz, 2H), 1.28 (s, 6H). MS (DCI) m/e: 338 (MH$^+$). IR (KBr): 2960, 1688, 1594, 1522. Anal. calcd. for C$_{24}$H$_{21}$N$_1$O$_4$. 0.350 H$_2$O: C, 73.21; H,5.56; N, 3.56. Found: C, 73.00; H, 5.43; N, 3.35.

EXAMPLE 24

3-Tributylstannylthiophene

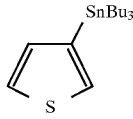

Using the method for the preparation of 3-tributylstannylfuran, 2.50 g (15.39 mmoles) of 3-bromothiophene gave 1.31 g (Y: 23%) of the title product. $^1$H NMR (CDCl$_3$): δ7.46 (m, 1H), 7.34 (d, J=2.3 Hz, 1H), 7.16 (d, J=4.6 Hz, 1H), 1.52 (m, 6H), 0.132 (m, 6H), 1.05 (t, J=8.2 Hz, 6H), 0.89 (t, J=7.2 Hz, 9H). MS (DCI) m/e: 375 (MH$^+$)

EXAMPLE 25

4-[[[(5,6,7,8-Tetrahydro-5,5-dimethyl-8-oxo)-2-napthalenyl]carbonyl]amino]benzoic acid, methyl ester (XVIa)

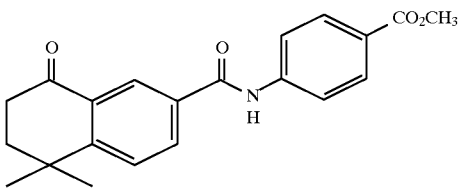

Using the method given for the preparation of the 8-(2-thienyl) derivative I¹a, 1.68 g (7.71 mmol) of compound XVa (compound of formula XV in which $R^a$ and $R^b$ are methyl) gave 2.10 g (Y: 78%) of the title product. ¹H NMR (CDCl₃): δ8.43 (d, J=2.1 Hz, 1H), 8.21 (dd, J=8.4, 2.1 Hz, 1H), 8.07 (d, J=8.7 Hz, 2H), 7.79 (d, J=8.7 Hz, 2H), 7.61 (d, J=8.4 Hz, 1H), 3.92 (s, 3H), 2.79 (t, J=6.5 Hz, 2H), 2.07 (t, J=6.5 Hz, 2H), 1.43 (s, 6H). MS (DCI) m/e: 352 (MH⁺)

EXAMPLE 26

4-[[[5,6-Dihydro-5,5-dimethyl-8-(trifluoromethanesulfonyloxy)]-2-napthalenyl]carbonyl]amino]benzoic acid, methyl ester (XXa)

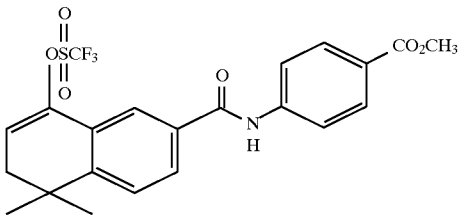

To a solution of compound XVIa (735 mg, 2.09 mmol) in tetrahydrofuran (10 mL) at −78° C. was added lithium diisopropylamide (1.0M solution in tetrahydrofuran, 4.61 mmol, 4.61 mL) and then N-(2-pyridyl)triflimide (2.30 mmol, 824 mg) at −78° C. Reaction mixture was stirred at −78° C. for 0.5 h and then warmed to room temperature. The reaction mixture was concentrated in vacuo and the residue chromatographed on silica gel (eluted with 10% ethyl acetate in hexane) to give 560 mg (Y: 55%) of the title product. ¹H NMR (CDCl₃): δ8.07 (d, J=8.7 Hz, 3H), 7.87 (m, 3H), 7.75 (d, J=8.7 Hz, 2H), 7.48 (d, J=8.0 Hz, 1H), 6.08 (t, J=4.5 Hz, 1H), 3.92 (s, 3H), 2.48 (d, J=4.5 Hz, 2H), 1.36 (s, 6H). MS (DCI) m/e 484 (MH⁺).

EXAMPLE 27

4-[[[5,6-Dihydro-5,5-dimethyl-8-(3-thienyl)]-2-naphthalenyl]carbonyl]amino]benzoic acid, methyl ester (I¹e)

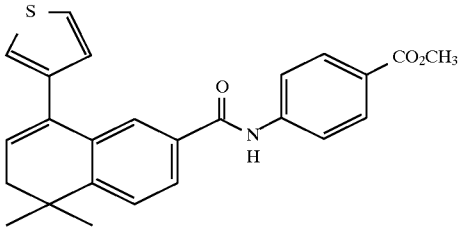

To a solution of compound XXa (125 mg, 0.26 mmol) in 1-methyl-2-pyrrolidinone (5 mL) at room temperature was added triphenylarsine (15 mg, 0.05 mmol), tris(dibenzylideneacetone) dipalladium (O) (7.4 mg, 0.008 mmol) and 3-tributylstannylthiophene (212 mg, 0.57 mmol) in 1-methyl-2-pyrrolidinone (1 mL). After 24 hours, water (20 mL) and ethyl acetate (20 mL) were added. The organic phase was separated and stirred over an aqueous saturated potassium fluoride solution for 30 minutes. The organic phase was again separated, concentrated in vacuo and the residue chromatographed on silica gel (eluted with 20% ethyl acetate in hexane) to give 78 mg (Y: 72%) of the title product. ¹H NMR (CDCl₃): δ8.03 (d, J=8.6 Hz, 2H), 7.79 (s, 1H), 7.74 (dd, J=7.9, 1.8 Hz, 1H), 7.67 (d, J=8.7 Hz, 2H), 7.49 (d, J=7.9 Hz, 1H), 7.39 (m, 1H), 7.28 (m, 1H), 7.13 (d, J=4.8 Hz, 1H), 6.17 (t, J=4.5 Hz, 1H), 3.91 (s, 3H), 2.37 (d, J=4.5 Hz, 2H), 1.36 (s, 6H). MS (DCI) m/e: 418 (MH⁺).

EXAMPLE 28

4-[[[[5,6-Dihydro-5,5-dimethyl-8-(3-thienyl)]-2-naphthalenyl]carbonyl]amino]benzoic acid (I²e)

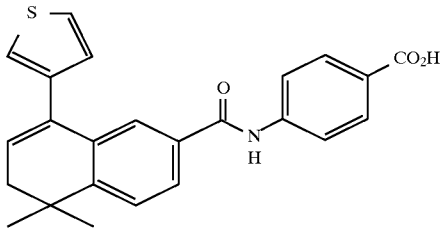

Using the method given for the preparation of the 8-(2-thienyl) derivative I²a, 78 mg (0.18 mmol) of compound I¹e gave 46 mg (Y: 61%) of the title product. ¹H NMR (DMSO): δ12.72 (s, 1H), 10.44 (s, 1H), 7.85 (m, 5H), 7.62 (m, 2H), 7.52 (m, 2H), 7.16 (dd, J=5.0, 1.3 Hz, 1H), 6.18 (t, J=4.5 Hz, 1H), 2.33 (d, J=4.5 Hz, 2H), 1.30 (s, 6H). MS (DCI) m/e: 404 (MH⁺). IR (KBr): 2960, 1688, 1594, 1520. Anal. calcd. for $C_{24}H_{21}O_3N_1S_1 \cdot 0.5\ H_2O$: C, 69.88; H, 5.38; N, 3.40. Found: C, 69.96, H, 5.05, N3.29.

EXAMPLE 29

N-[2-(Trimethylsilyl)ethoxymethyl]-4-[[[(5,6,7,8-tetrahydro-5,5-dimethyl-8-oxo)-2-naphthalenyl]carbonyl]amino]benzoic acid, methyl ester (XVIIa)

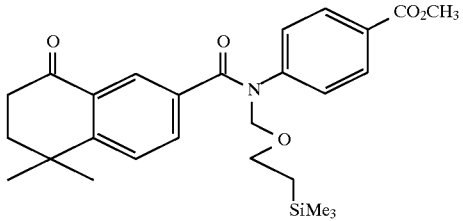

A solution of compound XVIa (3.45 g, 9.83 mmol) in anhydrous N,N-dimethylformamide (40 mL) at 0° C. was treated with 60% sodium hydride (433 mg, 10.8 mmol). When hydrogen evolution ceased 2-(trimethylsilyl)ethoxymethyl chloride (2.45 g, 14.73 mmol) was slowly added. After 16 h at room temperature, the mixture was diluted with a 10% sodium bicarbonate solution (100 mL) and extracted with diethyl ether. The organic phase was concentrated in vacuo and the residue chromatographed (eluted with 20% ethyl acetate in hexane) on silica gel to give 2.65 g (Y: 56%) of the title product. ¹H NMR (CDCl₃): δ8.02 (d, J=2.0 Hz, 1H), 7.92 (d, J=8.7 Hz, 2H), 7.54 (dd, J=8.2, 2.0 Hz, 1H), 7.31 (d, J=8.2 Hz, 1H), 7.23 (d, J=8.7 Hz, 2H), 5.28 (s, 2H), 3.89 (s, 3H), 3.69 (m, 2H), 2.67 (t, J=7.0

Hz, 2H), 1.97 (t, J=7.0 Hz, 2H), 1.35 (s, 6H), 0.97 (m, 2H), 0.00 (s, 9H). MS (DCI) m/e: 364 (M$^+$—OCH$_2$CH$_2$Si(CH$_3$)$_3$).

EXAMPLE 30

N-[2-(Trimethylsilyl)ethoxymethyl]-4-[[[[5,6,7,8-tetrahydro-5,5-dimethyl-8-(3-pyridinyl)-8-hydroxy]-2-naphthalenyl]amino]carbonyl]benzoic acid methyl ester (XVIIIa)

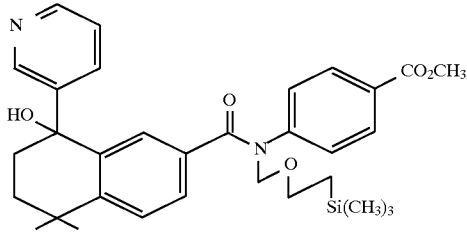

Using the method given for the preparation of the 8-(5-pyrimidinyl) derivative Xc, reaction of compound XVIIa (1.86 g, 3.87 mmol) and 3-pyridinyl lithium (0.32M solution in THF, 8.0 mmol, 25.0 ml; prepared by treating 3-bromopyridine in THF with n-butyllithium at −78° C.) gave 1.06 g (Y: 49%) of the title product. $^1$H NMR (CDCl$_3$): δ8.42 (dd, J=4.7, 1.6 Hz, 1H), 8.27 (dd, J=2.4, 0.8 Hz, 1H), 7.81 (d, J=8.8 Hz, 2H), 7.46 (dd, J=8.2, 2.0 Hz, 1H), 7.35 (d, J=8.4 Hz, 1H), 7.28 (m, 1H), 7.10 (m, 1H), 7.05 (d, J=8.8 Hz, 2H), 7.00 (d, J=1.8 Hz, 1H), 5.23 (m, 2H), 3.94 (s, 3H), 3.63 (m, 2H), 2.06 (m, 2H), 1.78 (m, 1H), 1.48 (m, 1H), 1.32 (s, 3H), 1.29 (s, 3H), 0.91 (m, 2H), 0.03 (s, 9H). MS (DCI) m/e: 431 (MH$^+$)

EXAMPLE 31

4-[[[[5,6,7,8-Tetrahydro-5,5-dimethyl-8-(3-pyridinyl)-8-hydroxyl-2-naphthalenyl]amino]carbonyl]benzoic acid, methyl ester (XIXa)

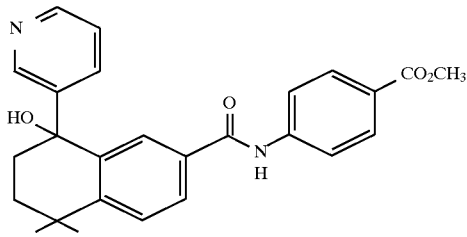

To a solution of compound XVIIIa (865 mg, 1.54 mmol) in absolute ethanol (15 mL) was added 1N hydrochloric acid (15 mL). The reaction mixture was stirred at 650° C. for 16 h and then cooled to room temperature. A saturated sodium bicarbonate solution was added and the mixture was then extracted with ethyl acetate (3×50 mL). The organic phases were then combined, concentrated in vacuo and the residue chromatographed on silica gel (eluted with 10% methyl alcohol in methylene chloride) to give 528 mg (Y: 80%) of the title product. $^1$H NMR (CDCl$_3$): δ8.47 (dd, J=4.1, 2.0 Hz, 1H), 8.41 (d, J=2.0 Hz, 1H), 8.25 (bs, 1H), 8.01 (d, J=8.7 Hz, 2H), 7.83 (dd, J=8.3, 2.0 Hz, 1H), 7.66 (d, J=8.7 Hz, 2H), 7.66 (s, 1H), 7.60 (m, 1H), 7.55 (d, J=8.2 Hz, 1H), 7.25 (m, 1H), 3.90 (s, 3H), 2.22 (m, 2H), 1.87 (m, 1H), 1.60 (m, 1H). 1.41 (s, 3H),1.38 (s,3H). MS (DCI) m/e: 431 (MH$^+$)

EXAMPLE 32

4-[[[[5,6-Dihydro-5,5-dimethyl-8-(3-pyridinyl)]-2-naphthalenyl]carbonyl]amino]benzoic acid, methyl ester (I$^1$f)

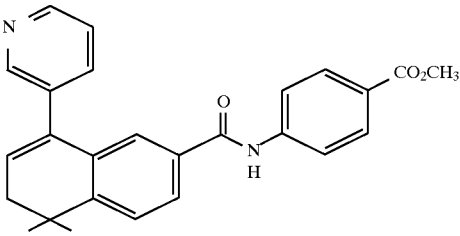

To a solution of compound XIXa (528 mg, 1.23 mmol) in toluene (12 mL) was added p-toluenesulfonic acid monohydrate (500 mg, 2.63 mmol). After heating at 90° C. for 2.5 h, the reaction mixture was concentrated in vacuo. The residue was diluted with saturated sodium bicarbonate (30 mL) and extracted with ethyl acetate (3×50 mL). The organic phases were combined, concentrated in vacuo and the residue chromatographed on silica gel (eluted with 10% methyl alcohol in methylene chloride) to give 390 mg (Y: 77%) of the title product. $^1$H NMR (CDCl$_3$): δ8.61 (m, 2H), 8.02 (d, J=8.7 Hz, 2H), 7.83 (s, 1H), 7.73 (dd, J=8.1, 1.0 Hz, 1H), 8.55 (d, J=8.7 Hz, 2H), 8.55 (m, 1H), 7.51 (d, J=8.0 Hz, 1H), 7.49 (d, J=1.9 Hz, 1H), 7.35 (m, 1H), 6.13 (t, J=4.5 Hz, 1H), 3.90 (s 3H), 2.43 (d, J=4.5 Hz, 2H), 1.39 (s, 6H). MS (DCI) m/e: 413 (MH$^+$)

EXAMPLE 33

4-[[[[5,6-Dihydro-5,5-dimethyl-8-(3-pyridinyl)]-2-naphthalenyl]carbonyl]amino]benzoic acid (I$^2$f)

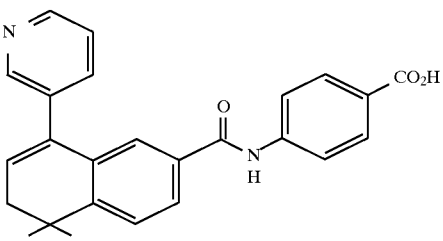

To a stirred solution of compound I$^1$f (1.09 g, 2.64 mmol) in a 1:1 ethanol and tetrahydrofuran solution (10 mL) was added 10N NaOH (27.0 mmol, 2.7 mL) at room temperature. After 24 hours, the reaction mixture was made neutral by the addition of 1N HCl and then concentrated in vacuo. The residue was then diluted with diethyl ether (heterogeneous mixture) and made acidic by the addition of gaseous HCl. After acidifying, the mixture was concentrated in vacuo and the residue chromatographed on C-18 silica gel (eluted salts with 100% water and product with 100% methanol) to give 540 mg (Y: 52%) of the title product. $^1$H NMR (DMSO): δ12.71 (bs, 1H), 10.43 (s, 1H), 8.58 (m, 2H), 7.80 (m, 6H), 7.56 (d, J=8.1 Hz, 1H), 7.46 (m, 1H), 7.38 (d, J=1.6 Hz, 1H), 6.18 (t, J=4.5 Hz, 1H), 2.38 (d, J=4.5Hz, 1H), 1.33 (s, 6H). MS (FAB) m/e: 399 (MH$^+$). IR (KBR): 3422, 2918, 1682, 1598. Anal. calcd. for C$_{25}$H$_{22}$N$_2$O$_3$·1.2 H$_2$O: C, 71.33; H, 5.87; N, 6.65. Found: C, 71.03; H, 5.74; N, 6.35.

EXAMPLE 34

1-Methyl-2-(tributylstannyl)pyrrole

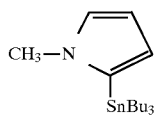

Prepared according to literature method of Bailey (*Tetrahedron Lett.*, 1986, 27, 4407–10).

EXAMPLE 35

4-[[[[5,6-Dihydro-5,5-dimethyl-8-(2-N-methylpyrrolyl)]-2-naphthalenyl]carbonyl]amino]benzoic acid, methyl ester ($I^1g$)

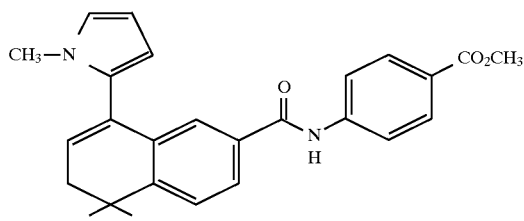

Using the method for the preparation of compound $I^1e$, 120 mg of compound XXa (0.248 mmol) gave 60 mg (Y: 58%) of the title product. $^1$H NMR (CDCl$_3$): δ8.03 (d, J=8.7 Hz, 2H), 7.78 (s, 1H), 7.74 (dd, J=8.2, 2.0 Hz, 1H), 7.67 (d, J=8.7 Hz, 2H), 7.48 (d, J=8.0 Hz, 1H), 6.70 (t, J=2.2 Hz, 1H), 6.19 (t, J=4.5 Hz, 1H), 6.15 (m, 2H), 3.91 (s, 3H), 3.39 (s, 3H), 2.40 (d, J=4.5 Hz, 2H), 1.38 (s, 6H). MS (DCI) m/e: 415 (MH$^+$)

EXAMPLE 36

4-[[[[5,6-Dihydro-5,5-dimethyl-8-(2-N-methylpyrolyl)]-2-naphthalenyl]carbonyl]amino]benzoic acid ($I^2g$)

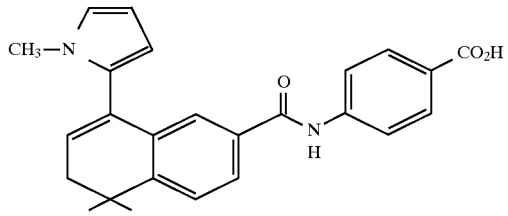

Using the method given for the preparation of the 8-(2-thienyl) derivative $I^2a$, 60 mg of compound $I^1g$ (0.145 mmol) gave 30 mg (Y: 52%) of the title product. $^1$H NMR (DMSO): δ10.45 (s, 1H), 7.84 (mn, 5H), 7.52 (d, J=8.1 Hz, 1H), 7.24 (d, J=1.9 Hz, 1H), 6.80 (t, J=2.2 Hz, 1H), 6.05 (mn, 3H), 3.33 (s 3H), 2.35 (d, J=4.5 Hz, 2H), 1.33 (s, 6H). MS (DCI) m/e: 401 (MH$^+$). IR (KBr) 2960, 1688, 1596, 1522, 1410. Anal. calcd. for C$_{25}$H$_{24}$N$_2$O$_3$·0.5 H$_2$O: C, 73.33; H, 6.15; N, 6.84. Found: C, 73.06; H, 6.02, N, 6.62.

EXAMPLE 37

4-[[[(5,6,7,8-Tetrahydro-5,5-dimethyl-8-oxo-2-naphthalenyl·carbonyl]N-tert-butoxycarbonyl-amin]benzoic acid, methyl ester (XVIIb)

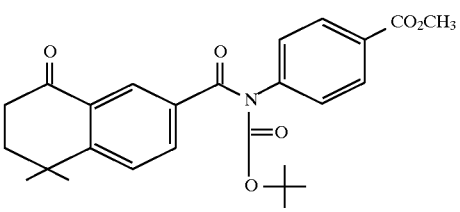

A solution of compound XVIa (4.66 g, 13.28 mmol) in anhydrous acetonitrile (22 mL) at room temperature was treated with 4-dimethylaminopyridine (200 mg, 1.62 mmol) followed by a solution of di-tert-butyldicarbonate (3.50 g, 15.0 mmol) in anhydrous acetonitrile (7 mL) in one portion with rapid stirring. After 16 h at room temperature, the mixture was concentrated in vacuo and the residue chromatographed (eluted with 20% ethyl acetate in hexane) on silica gel to give 4.29 g (Y: 72%) of the title product. $^1$H NMR (CDCl$_3$): δ8.34 (d, J=2.0 Hz, 1H), 8.11 (d, J=8.7 Hz, 2H), 7.90 (dd, J=8.0, 2.0 Hz, 1H), 7.53 (d, J=8.0 Hz, 1H), 7.32 (d, J=8.7 Hz, 2H), 3.93 (s, 3H), 2.77 (t, J=6.8 Hz, 2H), 2.08 (t, J=6.8 Hz, 2H), 1.43 (s, 6H), 1.26 (s, 9H). MS (DCI) m/e: 452 (MH$^+$).

EXAMPLE 38

4-[[[[5,6,7,8-Tetrahydro-5,5-dimethyl-8-(4-pyridinyl)-8-hydroxy]-2-naphthalenyl]carbonyl]N-tert-butoxycarbonylamino]benzoic acid, methyl ester (XVIIIb)

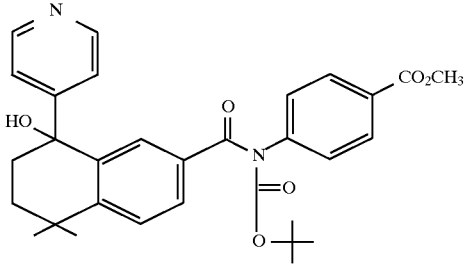

Using the method given for the preparation of the 8-(5-pyrimidinyl) derivative Xc, reaction of compound XVIII (1.01 g, 2.24 mmol) and 4-pyridinyl lithium (0.32M solution in THF, 3.4 mmol, 10.5 ml; prepared by treating 4-bromopyridine in THF with n-butyllithium at −78° C.) gave 168 mg (Y: 14%) of the title product. $^1$H NMR (CDCl$_3$): δ8.55 (d, J=6.3 Hz, 2H), 8.03 (d, J=8.4 Hz, 2H), 7.69 (dd, J=8.3, 2.0 Hz, 1H), 7.52 (d, J=8.3 Hz, 1H), 7.38 (d, J=6.3 Hz, 2H), 7.33 (d, J=2.0 Hz, 1H), 7.18 (d, J=8.4 Hz, 2H), 3.93 (s, 3H), 2.20–2.13 (m, 2H), 1.98–1.89 (m, 1H), 1.67–1.58(m, 1H), 1.42 (s, 3H), 1.38 (s, 3H), 1.24 (s, 9H). MS (IS) m/e: 531 (MH$^+$)

EXAMPLE 39

4-[[[[5,6,7,8-Tetrahydro-5,5-dimethyl-8-(4-pyridinyl)-8-hydroxy]-2-naphthalenyl]carbonyl]amino]benzoic acid, methy ester (XIXb)

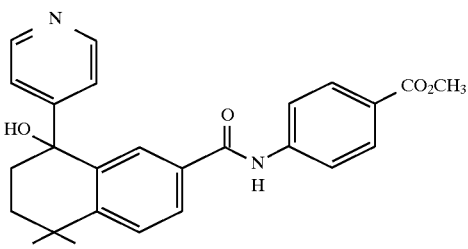

To a solution of compound XVIIIb (160 mg, 0.30 mmol) in methylene chloride (5 mL) was added a 90% solution of trifluoroacetic acid in methylene chloride (0.60 mL) at room temperature. After ½ h the reaction mixture was concentrated in vacuo to give 150 mg (Y: 99%) of the title product. $^1$H NMR (CDCl$_3$): δ9.04 (s, 1H), 8.53 (d, J=6.3 Hz, 2H), 7.84–7.68 (m, 5H), 7.57 (d, J=8.9 Hz, 2H), 7.53 (d, J=8.4 Hz, 1H), 7.46 (d, J=1.6 Hz, 1H), 3.84 (s, 3H), 2.22–1.96 (m, 3H), 1.62–1.54 (m, 0H), 1.38 (s, 3H), 1.34 (s, 3H) MS (IS) m/e: 431 (MH$^+$)

EXAMPLE 40

4-[[[[5,6-Dihydro-5,5-dimethyl-8-(4-pyridinyl)]-2-naphthalenyl]carbonyl]amino]benzoic acid, methyl ester (I$^1$h)

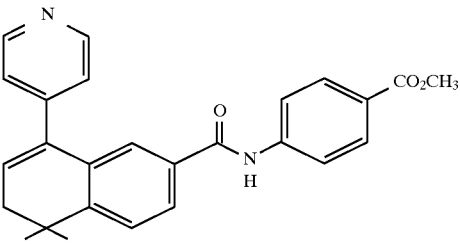

Using the method given for the preparation of the 8-(3-pyridinyl) derivative I$^2$f, 150 mg (0.35 mmol) of compound XIXb gave 82 mg (Y: 60%) of the title product. $^1$H NMR (CDCl$_3$): δ8.61 (d, J=6.2 Hz, 2H), 8.06 (bs, 1H), 8.01 (d, J=8.8 Hz, 2H), 7.78 (dd, J=8.1 Hz, 1H), 7.67 (d, J=8.8 Hz, 2H), 7.52–7.50 (m, 2H), 7.32 (d, J=6.2 Hz, 2H), 6.21 (t, J=4.5 Hz, 1H), 3.89 (s, 3H), 2.42 (d, J=4.5 Hz, 2H), 1.37 (s, 6H). MS (IS) m/e: 413 (MH$^+$)

EXAMPLE 41

4-[[[[5,6-Dihydro-5,5-dimethyl-8-(4-pyridinyl)]-2-naphthalenyl]carbonyl]amino]benzoic acid (I$^2$h)

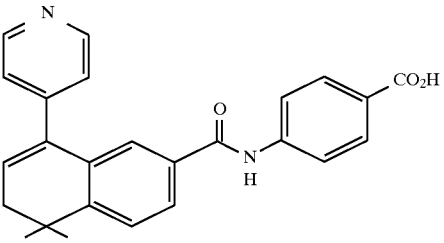

Using the method given for the preparation of the 8-(2-thienyl) derivative I$^2$a, 82 mg (0.20 mmol) of compound I$^1$h gave 30 mg (Y: 38%) of the title product. $^1$H NMR (DMSO): δ10.43 (s, 1H), 8.71 (d, J=6.2 Hz, 2H), 7.90 (d, J=8.2, 1.6 Hz, 1H), 7.88 (d, J=8.8 Hz, 2H), 7.81 (d, J=8.8 Hz, 2H), 7.61 (d, J=6.2 Hz, 2H), 7.58 (d, J=8.2 Hz, 1H), 7.44 (d, J=1.6 Hz, 1H), 6.38(t, J=4.5 Hz, 1H), 2.41 (d, J=4.5 Hz, 2H), 1.31 (s, 6H). MS (IS) m/e: 399 (MH$^+$). HRMS calculated: 399.1709. Found: 399.1706. 0.6 ppM deviation. IR (KBr): 3440, 2960, 1670, 1602.

EXAMPLE 42

4-[[[[5,6,7,8-Tetrahydro-5,5-dimethyl-8-[1-(2-trimethylsilanyl-ethoxymethyl)-2-imadazolyl]-8-hydroxy]-2-naphthalenyl]carbonyl]N-tert-butoxycarbonyl amino] benzoic acid, methyl ester

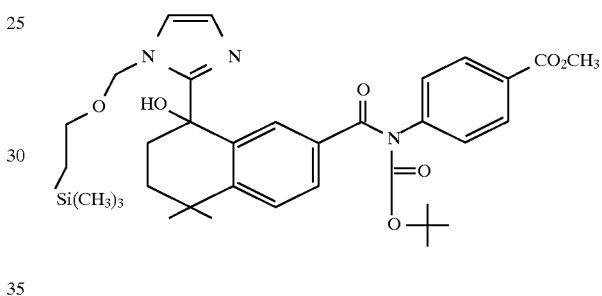

Using the method given for the preparation of the 8-(5-pyrimidinyl) derivative Xc, reaction of compound XVIIb (1.25 g, 2.76 mmol) and 1-(2-trimethylsilanylethoxymethyl)-2-imidazoyl lithium (0.30M solution in THF, 3.9 mmol, 13.0 ml; prepared by treating the protected imidazole with n-butyllithium at −78° C.) gave 560 mg (Y: 31%) of the title product. $^1$H NMR (CDCl$_3$): 8.01 (d, J=8.75 Hz, 2H), 7.67 (dd, J=8.2, 1.9 Hz, 1H), 7.49 (d, J=8.2 Hz, 1H), 7.15 (d, J=8.7 Hz, 2H), 7.13 (d, J=1.9 Hz, 1H), 7.03 (d, J=1.3 Hz, 1H), 6.93 (d, J=1.3 Hz, 1H), 5.18 (bs, 1H), 4.55–4.42 (m, 2H), 3.92 (s, 3H), 3.51–3.43 (m, 1H), 3.34–3.27 (m, 1H), 2.62–2.53 (m, 1H), 2.31–2.20 (m, 1H), 2.04–1.97 (m, 1H), 1.71–1.63 (m, 1H), 1.42 (s, 3H), 1.35 (s, 3H), 1.28 (s, 9H), 0.81 (m, 2H), 0.04 (s, 9H). MS (IS) m/e: 650 (MH$^+$).

EXAMPLE 43

4-[[[[5,6,7,8-Tetrahydro-5,5-dimethyl-8-[-(2-trimethylsilanyl-ethoxymethyl)-2-imadazolyl]-8-hydroxyl-2-naphthalenyl]carbonyl]amino]benzoic acid, methyl ester

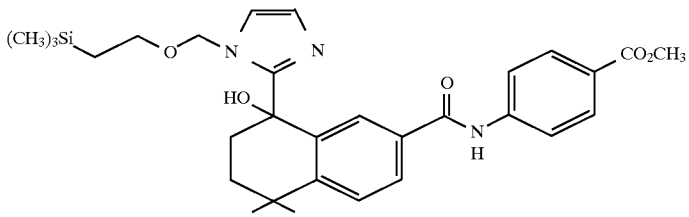

Using the method given for the preparation of the 8-(4-pyridinyl) derivative XIXb, 560 mg (0.86 mmol) of product from Example 42 gave 473 mg (Y: 99%) of the title product. $^1$H NMR (CDCl$_3$): δ9.23 (bs, 1H), 7.95–7.89 (m, 3H), 7.76–7.73 (m, 2H), 7.60–7.57 (m, 2H), 7.47 (bs, 1H), 7.23 (d, J=1.9 Hz, 1H), 4.83 (m, 2H), 3.88 (s, 3H), 3.56–3.48 (m, 1H), 3.40–3.31 (m, 1H), 2.50–2.38 (m, 2H), 2.27–2.18 (m, 1H), 1.68–1.62 (m, 1H), 1.39 (s, 3H), 1.36 (s, 3H), 0.83 (m, 2H), 0.04 (s, 9H). MS (IS) m/e: 550 (MH$^+$).

EXAMPLE 44

4-[[[[5,6,7,8-Tetrahydro-5,5-dimethyl-8-(2-imadazolyl)-8-hydroxy]-2-naphthalenyl]carbonyl]animo]benzoic acid, methyl ester (XIXc)

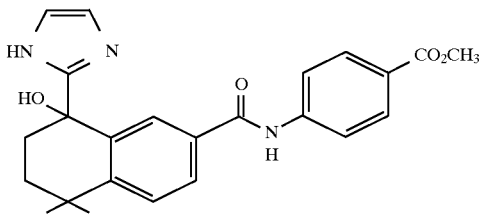

To a solution of compound made in Example 43 (473 mg, 0.86 mmol) in tetrahydrofuran (5 mL) was added tetrabutylammonium fluoride (5.17 mmol, 5.17 mL of a 1N solution in tehahydrofuran). After 16 h at reflux the reaction mixture was concentrated in vacuo, diluted with ethyl acetate (50 mL) and washed with water (50 mL×2). The organic phase was then dried through anhydrous sodium sulfate and concentrated in vacuo to give 215 mg (Y: 60%) of the title product. $^1$H NMR (CD$_3$OD): δ7.82–7.77 (m, 2H), 7.64–7.52 (m, 6H), 7.38 (d, J=8.4 Hz, 1H), 3.69 (s, 3H), 2.33–2.28 (m, 1H), 1.98–1.90 (m, 1H), 1.82–1.78 (m, 1H), 1.52–1.48 (m, 1H), 1.22 (s, 3H), 1.19 (s, 3H) MS (IS) m/e: 420 (MH$^+$).

EXAMPLE 45

4-[[[[5,6-Dihydro-5,5-dimethyl-8-(2-imadazolyl)]-2-naphthalenyl]carbonyl]amino]benzoic acid, methyl ester (I$^1$i)

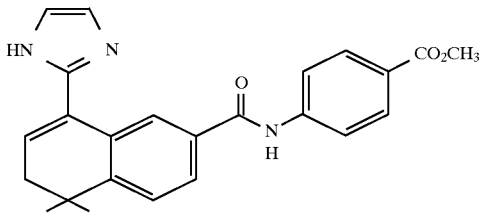

Using the method given for the preparation of the 8-(3-pyridinyl) derivative I$^1$f, 215 mg (0.51 mmol) of compound XIXC gave 94 mg (Y: 46%) of the title product. $^1$H NMR (CD$_3$OD): δ7.80–7.75 (m, 3H), 7.63–7.59 (m, 3H), 7.36 (d, J=8.2 Hz, 1H), 6.93–6.92 (m, 2H), 6.25 (t, J=4.5 Hz, 1H), 3.68 (3H), 2.24 (d, J=4.5 Hz, 2H), 1.15 (s, 6H). MS (DCI) m/e: 402 (MH$^+$).

EXAMPLE 46

4-[[[[5,6-Dihydro-5,5-dimethyl-8-(2-imadazolyl)]-2-naphthalenyl]carbonyl]amino]benzoic acid (I$^2$i)

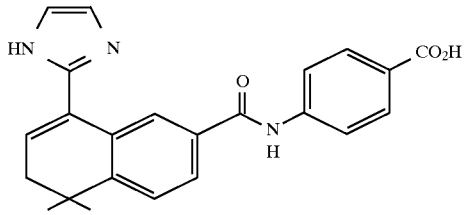

Using the method given for the preparation of the 8-(2-thienyl) derivative I$^2$a, 94 mg (0.23 mmol) of compound I$^1$i gave 49 mg (Y: 54%) of the title product. $^1$H NMR (DMSO): δ14.52 (bs, 1H), 12.72 (bs, 1H), 10.56 (s, 1H), 7.98–7.85 (m, 5H), 7.73 (s, 2H), 7.65 (s, 1H), 7.61 (d, J=8.1 Hz, 1H), 6.77 (t, J=4.5 Hz, 1H), 2.47 (d, J=4.5 Hz, 2H), 1.31 (s, 6H). MS (IS) 386 (MH$^-$). IR (KBr): 3432, 2962, 1684, 1596. Anal. calcd. for C$_{23}$H$_{21}$N$_3$O$_3$·1.0 H$_2$O·1.0 HCl 0.30 CH$_3$CO$_2$CH$_2$CH$_3$: C, 62.06; H, 5.68; N, 8.97. Found: C,62.33; H, 5.76; N, 8.60.

EXAMPLE 47

N-4-[[[[5,6,7,8-Tetrahydro-5,5-dimethyl-8-(4-isoquinolinyl)-8-hydroxyl]-2-napthalenyl]carbonyl]amino]benzoic acid, methyl ether (XVIIId)

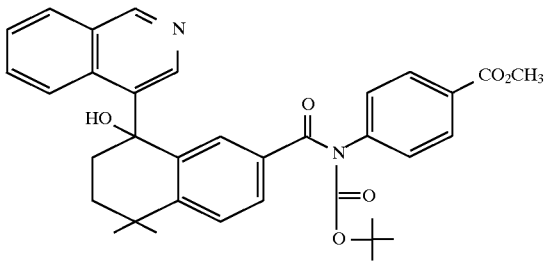

Using the method given for the preparation of the 8-(5-pyrimidinyl) derivative Xc, reaction of compound XVIIb (1.04 g, 2.31 mmol) and 4-isoquinolinyl lithium (0.30M solution in THF, 3.5 mmol, 11.6 ml; prepared by treating 4-bromoisoquinoline with n-butyllithium at −78° C.) gave 425 mg (Y: 32%) of the title product. $^1$H NMR (CDCl$_3$): δ9.38 (s, 1H), 8.20–8.17 (m, 2H), 7.88–7.85 (M, 3H), 7.74–7.70 (m, 3H), 7.63–7.61 (m, 2H), 7.04–7.01 (m, 2H), 3.92 (s, 3H), 2.63–2.53 (m, 2H), 2.15–2.07 (m, 1H), 1.69–1.53 (m, 1H), 1.50 (s, 3H), 1.31 (s, 3H), 1.22 (s, 9H). MS (IS) m/e: 581 (MH+).

EXAMPLE 48

4-[[[[5,6,7,8-Tetrahydro-5,5-dimethyl-8-(4-isoquinolinyl)-8-hydroxy]-2-naphthalenyl]carbonyl]amino]benzoic acid, methyl ester (XIXd)

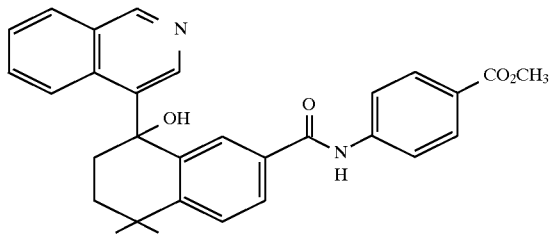

Using the method given for the preparation of the 8-(4-pyridinyl) derivative XIXb, 425 mg (0.73 mmol) of compound XVIIId gave 351 mg (Y: 99%) of the title product. $^1$H NMR (CDCl$_3$): δ9.35 (m, 1H), 7.89–7.64 (m, 5H), 7.29–7.16 (m, 7H), 3.82 (s, 3H), 2.56–2.42 (m, 2H), 2.12–2.07 (m, 1H), 1.75–1.70 (m, $^1$H), 1.52 (s, 3H), 1.51 (s, 3H). MS (IS) m/e: 481 (MH+)

EXAMPLE 49

4-[[[[5,6-Dihydro-5,5-dimethyl-8-(4-isoquinolinyl)]-2-naphthalenyl]carbonyl]amino]benzoic acid, methyl ester (I$^1$j)

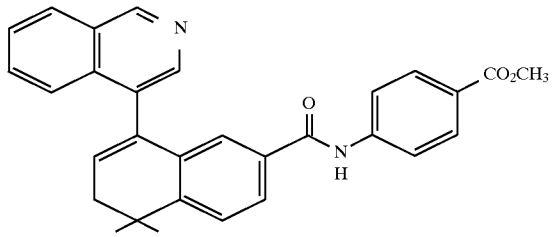

Using the method given for the preparation of the 8-(3-pyridinyl) derivative $^1$f, 351 mg (0.73 mmol) of compound XIXd gave 280 mg (Y: 83%) of the title product. $^1$H NMR (CDCl$_3$): δ9.31 (s, 1H), 8.47 (s, 1H), 8.12 (t, J=4.0 Hz, 1H), 8.02 (d, J=1.8 Hz, 1H), 7.92 (d, J=8.8 Hz, 2H), 7.79 (dd, J=8.0, 1.9 Hz, 1H), 7.72–7.67 (m, 3H), 7.57 (d, J=8.8 Hz, 2H), 7.07 (d, J=1.9 Hz, 1H), 6.22 (dt, J=3.7, 1.6 Hz, 1H), 3.86 (s, 3H), 2.54 (m, 2H), 1.52 (s, 3H), 1.47 (s, 3H). MS (DCI) m/e: 463 (MH+).

EXAMPLE 50

4-[[[[5,6-Dihydro-5,5-dimethyl-8-(4-isoquinolinyl)]-2-naphthalenyl]carbonyl]amino]benzoic acid (I$^2$j)

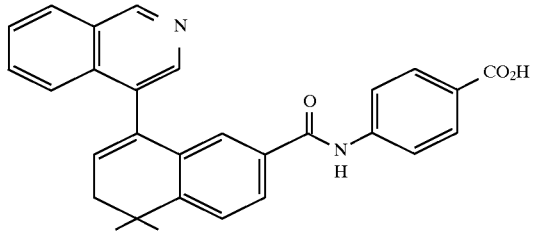

Using the method given for the preparation of the 8-(2-thienyl) derivative I$^2$a, 280 mg (0.61 mmol) of compound I$^1$j gave 240 mg (Y: 88%) of the title product. $^1$H NMR (DMSO): δ10.39 (s, 1H), 9.85 (s, 1H), 8.64 (s, 1H), 8.54 (d, J=8.0 Hz, 1H), 8.05–7.89 (m, 3H), 7.81 (d, J=8.5 Hz, 2H), 7.75 (m, 1H), 7.72 (d, J=8.5 Hz, 2H), 7.63 (d, J=8.0 Hz 1H), 6.96 (s, 1H), 6.33 (t, J=4.5 Hz, 1H), 2.53 (d, J=4.5 Hz, 2H), 1.48 (s, 3H), 1.42 (s, 3H). MS (DCI) m/e: 449 (MH+). IR (KBr): 3420, 2960, 1699, 1594, 1524. Anal. calcd. for C$_{29}$H$_{24}$N$_2$O$_3$·1.0 HCl·1.25 H$_2$O: C, 68.63; H, 5.46; N, 5.52. Found: C, 68.63; H, 5.65; N, 5.20.

EXAMPLE 51

N-4-[[[[5,6,7,8-Tetrahydro-5,5-dimethyl-8-(3-quinolinyl)-8-hydroxy]-2-naphthalenyl]carbonyl]amino]benzoic acid, methyl ester (XVIIIe)

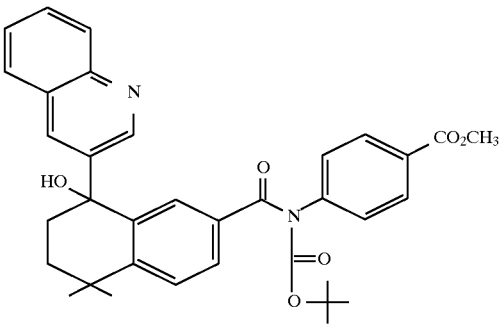

Using the method given for the preparation of the 8-(5-pyrimidinyl) derivative Xc, reaction of compound XVIIb (865 mg, 1.92 mmol) and 3-quinolinyl lithium (0.30M solution in THF, 2.88 mmol, 9.6 ml; prepared by treating 3-bromoquinoline with n-butyllithiym at −78° C.) gave 352 mg (Y: 32%) of the title product. $^1$H NMR (CDCl$_3$): δ8.8 (d, J=2.2 Hz, 1H), 7.97 (d, J=8.7 Hz, 2H), 7.99–7.96 (m, 1H), 7.80–7.69 (m, 3H), 7.58–7.52 (m, 3H), 7.16 (d, J=8.7 Hz, 2H), 7.17–7.14 (m, 1H), 3.90 (s, 3H), 2.38–2.21 (m, 2H), 1.97–1.88 (m, 1H), 1.67–1.60 (m, 1H), 1.45 (s, 3H), 1.40 (s, 3H), 1.18 (s, 9H). MS (IS) m/e: 581 (MH+).

EXAMPLE 52

4-[[[[5,6,7,8-Tetrahydro-5,5-dimethyl-8-(3-quinolinyl)-8-hydroxyl-2-naphthalenyl]naphthalenyl]carbonyl]amino]benzoic acid, methyl ester (XIXe)

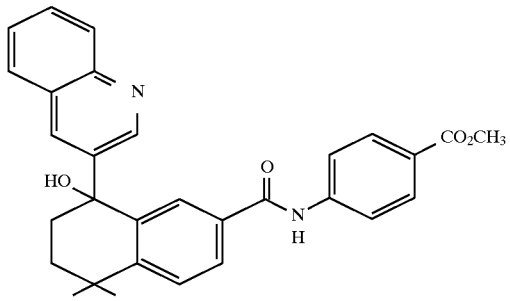

Using the method given for the preparation of the 8-(4-pyridinyl) derivative XIXb, 350 mg (0.60 mmol) of compound XIXb gave 289 mg (Y: 99%) of the title product. $^1$H NMR (CDCl$_3$): δ9.50 (d, J=1.7 Hz, 1H), 9.29 (s, 1H), 8.32–8.29 (m, 3H), 7.98–7.75 (m, 7H), 7.61–7.56 (m, 3H), 3.85 (s, 3H), 2.41–2.32 (m, 1H), 2.17–2.08 (m, 1H), 1.99–1.91 (m, 1H), 1.58–1.49 (m, 1H), 1.40 (s, 6H). MS (IS) m/e: 481 (MH$^+$).

EXAMPLE 53

4-[[[[5,6-Dihydro-5,5-dimethyl-8-(3-quinolinyl)]-2-naphthalenyl]carbonyl]amino]benzoic acid, methyl ester (I$^1$k)

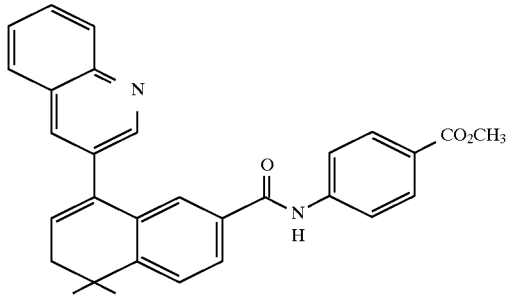

Using the method given for the preparation of the 8-(3-pyridinyl) derivative I$^1$f, 289 mg (0.60 mmol) of compound XIXe gave 254 mg (Y: 91%) of the title product. $^1$H NMR (CDCl$_3$): δ8.88 (dd, J=2.0 Hz, 1H), 8.18 (dd, J=2.0 Hz, 1H), 8.14 (d, J=8.4 Hz, 1H), 8.03 (d, J=1.1 Hz, 1H), 7.94 (d, J=8.8 Hz, 2H), 7.93–7.71 (m, 3H), 7.61 (d, J=8.8 Hz, 2H), 7.60–7.26 (m, 3H), 6.22 (t, J=4.5 Hz, 1H), 3.87 (s, 3H), 2.47 (d, J=4.5 Hz, 2H), 1.27 (s, 6H). MS (IS) in/e: 463 (MH$^+$).

EXAMPLE 54

4-[[[[5,6-Dihydro-5,5-dimethyl-8-(3-quinolinyl)]-2-naphthalenyl]carbonyl]amino]benzoic acid (I$^2$k)

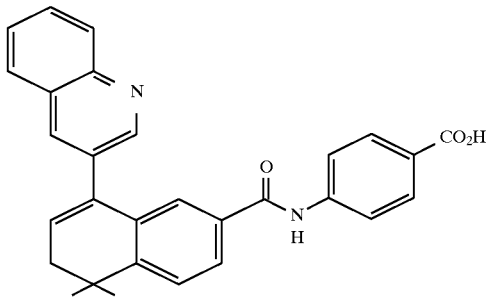

Using the method given for the preparation of the 8-(2-thienyl) derivative I$^2$a, 254 mg (0.55 mmol) of compound I$^1$k gave 185 mg (Y: 75%) of the title product. $^1$H NMR (DMSO): δ10.44 (s, 1H), 9.18 (d, J=1.8 Hz, 1H), 8.84 (s, 1H), 8.23 (d, J=8.5 Hz, 2H), 7.99 (d, J=7.3 Hz, 1H), 7.93 (dd, J=8.1, 1.8 Hz, 1H), 7.86–7.76 (m, 5H), 7.61 (d, J=8.1 Hz, 1H), 7.50 (d, J=1.8 Hz, 1H), 6.41 (t, J=4.5 Hz, 1H), 2.46 (d, J=4.5 Hz, 2H), 1.37 (s, 6H). MS (DCI) m/e: 449 (MH$^+$). IR (KBr): 3420, 1702, 1656, 1594. Anal. calcd. for $C_{29}H_{24}N_2O_3 \cdot 1.5 H_2O$: C, 68.03; H, 5.51; N, 5.47. Found: C, 67.71; H, 5.52; N, 5.10.

EXAMPLE 55

N-[2-(Trimethylsilyl)ethoxymethyl]-4-[[[[5,6,7,8-tetrahydro -5,5-dimethyl-8-(2-thiazolyl)-8-hydroxyl-2-naphthalenyl]carbonyl]amino]benzoic acid, methyl ester (XVIIIf)

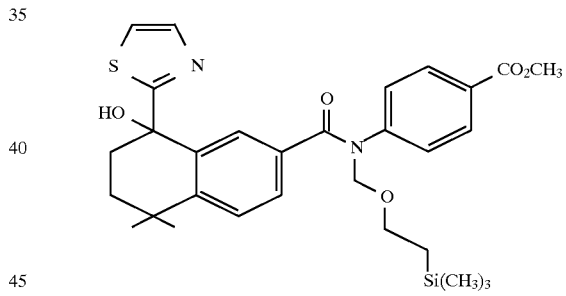

Using the method given for the preparation of the 8-(5-pyrimidinyl) derivative Xc, reaction of compound XVIIa (1.62 g, 3.37 inmol) and 2-thiazolyl lithium (0.32M solution in THF, 15.0 ml, 4.8 mmol; prepared by treating 2-bromothiazole with n-butyllithium at −78° C.) gave 497 mg (Y: 26%) of the title product. $^1$H NMR (CDCl$_3$): 7.82 (d, J=8.4 Hz, 2H), 7.66 (d, J=3.3 Hz, 1H), 7.47 (dd, J=8.2 Hz, 1.5 Hz, 1H), 7.32 (d, J=8.2 Hz, 1H), 7.20 (d, J=1.5 Hz, 1H), 7.17 (d,J=3.3 Hz, 1H), 7.10 (d, J=8.4 Hz, 2H), 5.29 (d, J=10.0 Hz, 1H), 5.14 (d, J=10.0 Hz, 1H), 3.91 (s, 3H), 3.72–3.61 (m, 2H), 2.42–2.34 (m, 1H), 2.25–2.14 (m, 1H), 1.88–1.80 (m, 1H), 1.73–1.64 (m, 1H), 1.31 (s, 6H), 0.98–0.92 (m, 2H), 0.00 (s, 9H). MS (DCI) m/e: 567 (MH$^+$).

EXAMPLE 56

4-[[[[5,6,7,8-Tetrahydro-5,5-dimethyl-8-(2-thiazolyl)-8-hydroxyl -2-naphthalenyl]carbonyl]amino]benzoic acid, methyl ester (XIXf)

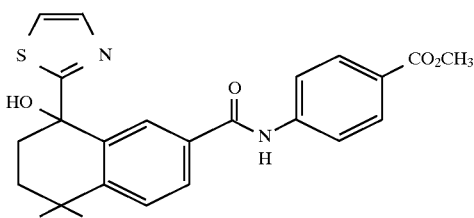

Using the method given for the preparation of the 8-(3-pyridinyl) derivative XIXa, 497 mg (0.88 mmol) of compound XVIIIf gave 126 mg (Y: 33%) of the title product. $^1$H NMR (CDCl$_3$): δ8.05 (d, J=8.5 Hz, 2H), 7.88–7.82 (m, 2H), 7.80 (d, J=3.3 Hz, 1H), 7.69 (d, J=8.5 Hz, 2H), 7.54 (d, J=8.2 Hz, 1H), 7.33 (d, J=3.3 Hz, 1H), 3.90 (s, 3H), 2.53–2.48 (m, 1H), 2.39–2.29 (m, 1H), 2.02–1.92 (m, 1H), 1.88–1.78 (m, 1H), 1.39 (s, 6H). MS (DCI) m/e: 437 (MH$^+$).

EXAMPLE 57

4-[[[[5,6-Dihydro-5,5-dimethyl-8-(2-thiazolyl)1-2-naphthalenyl]carbonyll aminol benzoic acid, methyl ester (I$^1$m)

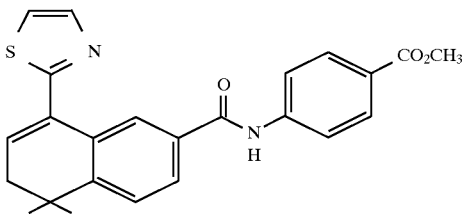

Using the method given for the preparation of the 8-(2-thienyl) derivative I$^2$a, 126 mg (0.29 mmol) of compound XIXf gave 44 mg (Y: 36%) of the title product. $^1$H NMR (CDCl$_3$): δ8.29 (d, J=1.9 Hz, 1H), 8.17 (bs, 1H), 8.04 (d, J=8.8 Hz, 2H), 7.91 (d, J=3.3 Hz, 1H), 7.83 (dd, J=8.1, 1.9 Hz, 1H), 7.73 (d, J=8.8 Hz, 2H), 7.50 (d, J=8.1 Hz, 1H), 7.33 (d, J=3.3 Hz, 1H), 6.65 (t, J=4.5 Hz, 1H), 3.91 (s, 3H), 2.44 (d, J=4.5 Hz, 2H), 1.36 (s, 6H). MS (DCI) m/e: 491 (MH$^+$).

EXAMPLE 58

4-[[[[5,6-Dihydro-5,5-dimethyl-8-(2-thiazolvl)]-2-naphthalenyl]carbonyl]amino]benzoic acid (I$^2$m)

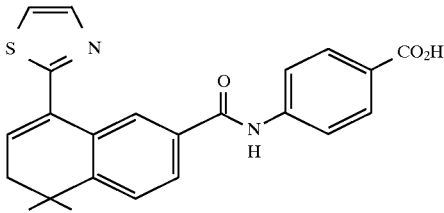

Using the method given for the preparation of the 8-(2-thienyl) derivative I$^2$a, 44 mg (0.10 mmol) of compound I$^1$m gave 14 mg (Y: 33%) of the title product. $^1$H NMR (DMSO): δ10.47 (s, 1H), 8.25 (d, J=1.7 Hz, 1H), 7.94–7.83 (m, 6H), 7.75 (d, J=3.3 Hz, 1H), 7.55 (d, J=8.1 Hz, 1H), 6.67 (t, J=4.5 Hz, 1H), 2.41 (d, J=4.5 Hz, 2H), 1.29 (s, 6H). MS (IS) m/e: 403 (MH$^-$). IR (KBr): 3432, 1684, 1596, 1528. Anal. calcd. for C$_{23}$H$_{20}$N$_2$O$_3$S, ·0.50 H$_2$O: C, 61.40; H. 4.93; N, 6.23. Found C, 61.64; H, 5.21; N, 5.96.

EXAMPLE 59

N-[2-(Trimethylsilyl)ethoxymethyl]-4-[[[[5,6,7,8-tetrahydro -5,5-dimethyl-8-(2-pyridinyl)-8-hydroxyl-2-naphthalenyl]carbonyl]amino]benzoic acid, methyl ester (XVIIIg)

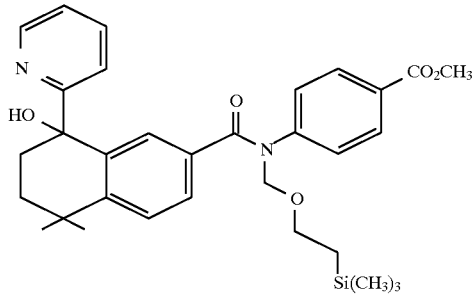

Using the method given for the preparation of the 8-(5-pyrimidinyl) derivative Xc, reaction of compound XVIIa (1.15 g, 2.39 mmol) and 2-pyridinyl lithium (0.32M solution in THF, 14.9 ml, 4.8 mmol; prepared by treating 2-bromopyridine with n-butyllithium at −78° C.) gave 470 mg (Y: 35%) of the title product. $^1$H NMR (CDCl$_3$): δ8.52–8.50 (m, 1H), 7.75 (d, J=8.7 Hz, 2H), 7.44–7.41 (m, 2H), 7.32 (d, J=8.4 Hz, 1H), 7.19–7.13 (m, 1H), 7.04 (d, J=8.7 Hz, 2H), 6.79 (d, J=1.9 Hz, 1H), 6.48 (d, J=8.0 Hz, 1H), 5.29 (d, J=10.0 Hz, 1H), 5.04 (d, J=10.0 Hz, 1H), 3.93 (s, 3H), 3.69–3.54 (m, 2H), 2.07–2.03 (m, 2H), 1.95–1.83 (m, 1H), 1.60–1.50 (m, 1H), 1.34 (s, 3H), 1.32 (s, 3H), 0.93–0.87 (m, 2H), 0.03 (s, 9H). MS (DCI) m/e: 561 (MH$^+$)

EXAMPLE 60

4-[[[[5,6,7,8-Tetrahydro-5,5-dimethyl-8-(2-pyridinyl)-8-hydroxyl]-2-naphthalenyl]carbonyl]amino]benzoic acid, methyl ester (XIXg)

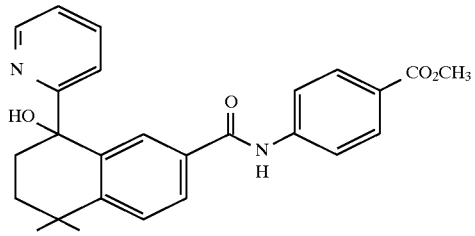

Using the method given for the preparation of the 8-(3-pyridinyl) derivative XIXa, 470 mg (0.84 mmol) of compound XVIIIa gave 208 mg (Y: 58%) of the title product. $^1$H NMR (CDCl$_3$): δ8.62 (dd, J=4.6, 0.9 Hz, 1H), 7.99 (d, J=8.7 Hz, 2H), 7.91 (bs, 1H), 7.81 (dd, J=8.4 Hz, 2.1 Hz, 1H), 7.66 (d, J=8.7 Hz, 2H), 7.63–7.59 (m, 2H), 7.56 (d, J=8.4 Hz, 1H), 7.48 (d, J=2.1 Hz, 1H), 6.80 (d, J=8.0 Hz, 1H), 3.89 (s, 3H), 2.20–2.15 (m, 2H), 2.07–1.92 (m, 1H), 1.72–1.63 (m, 1H), 1.43 (s, 3H), 1.42 (s, 3H). MS (DCI) m/e: 431 (MH$^+$).

EXAMPLE 61

4-[[[[5,6-Dihydro-5,5-dimethyl-8-(2-pyridinyl)·-2-npahthalenyl]carbonyl]amino]benzoic acid, methyl ester (I$^1$n)

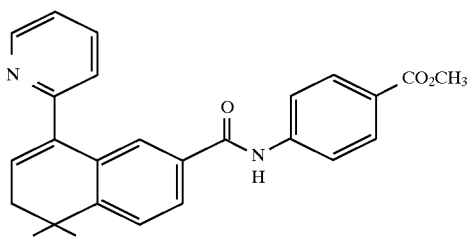

Using the method given for the preparation of the 8-(3-pyridinyl) derivative I¹f, 208 mg (0.48 mmol) of compound XIXq gave 62 mg (Y: 31%) of the title product. ¹H NMR (CDCl$_3$): δ8.72–8.68 (m, 1H), 8.02 (d, J=8.7 Hz, 2H), 7.81–7.72 (m, 2H), 7.67 (d, J=8.7 Hz, 2H), 7.64 (d, J=1.9Hz, 1H), 7.50 (d, J=8.2 Hz, 1H), 7.46 (m, 1H), 7.32–7.28 (m, 1H), 6.38 (t, J=4.5 Hz, 1H), 3.90 (s, 3H), 2.44 (d, J=4.5 Hz, 2H), 1.38 (s, 6H) MS (DCI) m/e: 413 (MH⁺)

EXAMPLE 62

4-[[[[5,6-Dihydro-5,5-dimethyl-8-(2-pyridinyl)1-2-naphthalenyl]carbonyl]amino]benzoic acid (I²n)

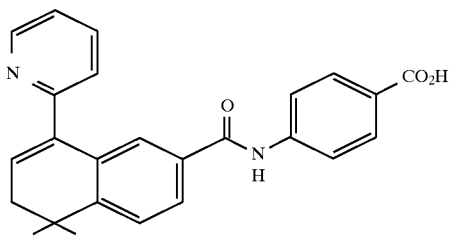

Using the method given for the preparation of the 8-(2-thienyl) derivative I²a, 62 mg (0.15 mmol) of compound I¹n gave 47 mg (Y: 78%) of the title product. ¹H NMR (CDCl$_3$): δ9.24 (bs, 1H), 8.69 (d, J=4.5 Hz, 1H), 7.89(m, 1H), 7.88 (d, J=8.7 Hz, 2H), 7.79 (d, J=8.7 Hz, 2H), 7.66 (d, J=8.0 Hz, 1H), 7.52 (d, J=8.0 Hz, 1H), 7.49–7.38 (m, 3H), 6.33 (t, J=4.5 Hz, 1H), 2.40 (d, J=4.5 Hz, 2H), 1.33 (s, 6H). MS (DCI) m/e: 399 (MH⁺). IR (KBr): 3445, 2960, 1680, 1596. Anal. calcd. for C$_{25}$H$_{22}$N$_2$O$_3$·1.25 H$_2$O: C, 71.33; H, 5.87; N, 6.65. Found: C, 71.48; H, 5.95; N, 6.24.

EXAMPLE 63

4,4-Dimethyl-7-iodo-1-tetralone (XXIIa)

To a solution of 4,4-dimethyl-7-amino-1-tetralone (XXIa) (1.82 g, 10.0 mmol) in concentrated hydrochloric acid (4.69 mL) was added ice cold water (3.13 mL). The reaction mixture was then cooled to 0° C. by use of an ice-salt bath. The reaction mixture was then diazotized by the dropwise addition with stirring of a solution of sodium nitrite (0.76 g, 11.0 mmol) in water (3.13 mL) keeping temperature between 0°–5° C. After stirring for 15 minutes, the reaction mixture was added to a solution of potassium iodide (3.63 g, 21.9 mmol) in water (18.8 mL). After standing for 30 minutes, the dark gum was extracted with ethyl acetate (1×100 mL). The organic phase was then concentrated in vacuo and the residue chromatographed on silica gel (eluted with 5% ethyl acetate in hexane) to give 1.56 g (Y: 54%) of the title product. ¹H-NMR (CDCl$_3$): δ8.33 (d, J=2.0 Hz, 1H), 7.82 (dd, J=8.3, 2.0 Hz, 1H), 7.17 (d, J=8.4 Hz, 1H), 2.72 (t, J=6.8 Hz, 2H), 2.01 (t, J=6.8 Hz, 2H), 1.37 (s, 6H) ; MS (DCI) m/e: 301 (MH⁺).

EXAMPLE 64

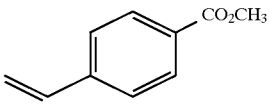

To a solution of 4-vinylbenzoic acid (Aldrich, 2.18 g, 14.7 mmol) in anhydrous acetonitrile (14.0 mL) was added 1,8-diazabicyclo [5.4.0]undec-7-ene (Aldrich, 2.46 g, 16.2 mmol) and iodomethane (Aldrich, 3.13g, 22.1 mmol) at 0° C. The reaction mixture was then warmed to room temperatue and allowed to stir for 3 h. Ethyl acetate (100 mL) was added to the mixture and the solution was washed with brine (50 mL). The organic phase was then separated and concentrated in vacuo. The residue was chromatographed on silica gel (eluted with 5% ethyl acetate in hexane) to give 1.05 g (Y: 44%) of the title product. ¹H-NMR (CDCl$_3$): δ8.00 (d,J=8.4 Hz, 2H), 7.47 (d, J=8.4 Hz, 2H), 6.76 (m, 1H), 5.87 (d, J=17.6 Hz, 1H), 5.38 (d, J=11.0 Hz, 1H), 3.91 (s, 3H); MS (DCI) m/e: 163 (MH⁺).

EXAMPLE 65

4-[[(E)-(5,6,7,8-Tetrahydro-5,5-dimethyl-8-oxo)-2-naphthalenyl]ethenyl]benzoic acid, methyl ester (XXIIIa)

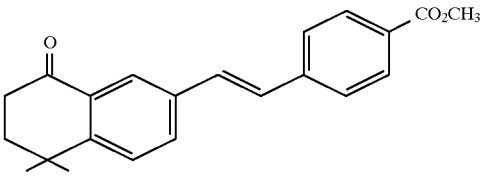

To a solution of 4,4-dimethyl-7-iodo-1-tetralone (XXIIa) (1.55 g, 5.17 mmol) and methyl 4-vinylbenzoate (1.67 g, 10.34 mmol) in dimethylformamide (16.0 mL) was added palladium (II) acetate (Aldrich, 58 mg, 0.259 mmol), tetrabutylammonium chloride hydrate (Aldrich, 1.49 g, 5.17 mmol) and sodium bicarbonate (Mallinckrodt, 1.09 g, 12.9 mmol). The reaction mixture was heated to 70° C. for 4 h and then allowed to stir at room temperature for 16 h. Ethyl acetate (50 mL) was added to the mixture and the solution was washed with brine (50 mL). The organic phase was concentrated in vacuo and the residue chromatographed on silica gel (eluted with 10% ethyl acetate in hexane) to give 1.29 g (Y: 75%) of the title compound. ¹H-NMR (CDCl$_3$): δ8.19 (d, J=1.7 Hz, 1H), 8.04 (d, J=8.2 Hz, 2H), 6.69 (dd, J=8.1, 1.7 Hz, 1H), 7.57 (d, J=8.2 Hz, 2H), 7.45 (d, J=8.1 Hz, 1H), 7.21 (s, 2H), 3.93 (s, 3H), 2.76 (t, J=6.8 Hz, 2H), 2.05 (t, J=6.8 Hz, 2H), 1.41 (s, 6H); MS (DCI) m/e: 335 (MH⁺)

EXAMPLE 66

4-[[(E)-[5,6,7,8-Tetrahydro-5,5-dimethyl-8-(3-pyridinyl)-8-hydroxy]-2-naphthalenyl]ethenyl]benzoic acid, methyl ester (XXIVa)

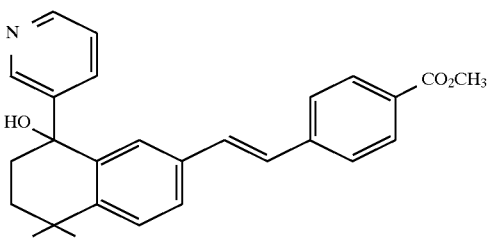

Using the method for the preparation of the 8-(5-pyrinidinyl) derivative Xc, reaction of compound XXIIIa (1.31 g, 3.93 mmol) and 3-pyridinyl lithium (0.32M solution in THF, 25.0 ml, 8.0 mmol; prepared by treating 3-bromopyridine with n-butyllithium at −78° C.) gave 881 mg (Y: 54%) of the title product. $^1$H-NMR (CDCl$_3$): δ8.55 (d, J=3.1 Hz, 1H), 8.50 (d, J=6.4 Hz, 1H), 7.97 (d, J=8.1 Hz, 2H), 7.66 (dd, J=8.0, 1.8 Hz, 1H), 7.49–7.42 (m, 4H), 7.26–7.21 (m, 2H), 7.06 (d, J=16.4 Hz, 1H), 6.96 (d, J=16.4 Hz, 1H), 3.91 (s, 3H), 2.22–2.18 (m, 2H), 1.94–1.85 (m, 1H), 1.61–1.53 (m, 1H), 1.40 (s, 3H), 1.36 (s, 3H); MS (DCI) m/e: 414 (MH$^+$)

EXAMPLE 67

4-[[(E)-[5,6-Dihydro-5,5-dimethyl-8-(3-pyridinyl)-2-naphthalenyl]ethenyl]benzoic acid, methyl ester (I$^3$a)

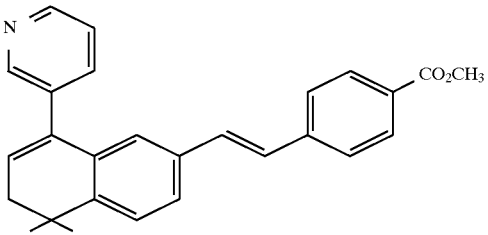

Using the method for the preparation of the 8-(3-pyrindyl) derivative I$^1$f, 880 mg (2.13 mmol) of compound I$^3$a gave 709 mg (Y: 84%) of the title compound. $^1$H-NMR (CDCl$_3$): δ8.66–8.63 (m, 2H), 7.98 (d, J=8.1 Hz, 2H), 7.73 (dd, J=8.0, 1.8 Hz, 1H), 7.49 (d, J=8.1 Hz, 2H), 7.45 (d, J=1.8 Hz, 1H), 7.41–7.39 (m, 2H), 7.09 (d, J=16.4 Hz, 1H), 7.06 (s, 1H), 6.88 (d, J=16.4 Hz, 1H), 6.08 (t J=4.5 Hz, 1H), 3.91 (s, 3H), 2.40 (d, J=4.5Hz, 2H), 1.36 (s, 6H); MS (DCI) m/e: 396 (MH$^+$)

EXAMPLE 68

4-[[(E)-[5,6-Dihydro-5-5-dimethyl-8-(3-pyridinyl)-2-naphthalenyl]ethenyl-9 benzoic acid (I$^4$a)

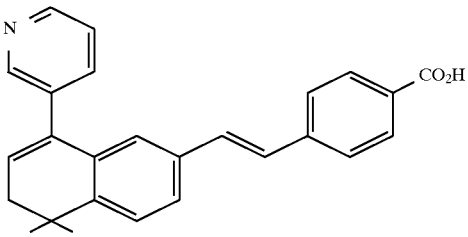

To a solution of compound I$^3$a (709 mg, 1.79 mmol) in ethyl alcohol (10 ml) and tetrahydrofuran (3 ml) was added 10N NaOH (25.0 mmol, 2.50 ml) at 70° C. After ¼ h, an excess of 1N HCl (50 ml) was added and the precipitate collected by vacuum filtration. The solid was chromatographed on silica gel (eluted with 10% methyl alcohol in methylene chloride) to give 560 mg (Y: 82%) of the title product. $^1$H-NMR (DMSO): δ8.94–8.92 (m, 2H), 8.53 (d, J=8.1 Hz, 1H), 8.11–8.06 (m,1H), 7.87 (d, J=8.1 Hz, 2H), 7.61 (d, J=1.8 Hz, 2H), 7.60 (m, 1H), 7.45 (d, J=8.1 Hz, 1H), 7.30 (d, J=16.4 Hz, 1H), 7.16 (d J=16.4 Hz, 1H), 7.08 (s, 1H), 6.32 (t, J=4.5 Hz, 1H), 2.38(d, J=4.5 Hz, 2H), 1.30 (s, 6 H); MS (DCI) m/e: 382 (MH$^+$); IR (KBr): 3424, 2956, 1680, 1604 cm$^{-1}$; Anal. calc. for $C_{26}H_{22}N_1O_2$ ·1.0 HCl·1.0 H$_2$O: C, 71.80; H, 5.79; N, 3.22. Found: C, 72.12; H, 5.75; N, 3.09.

This invention is further illustrated by the following biological tests, which are illustrative only.

Rhino Mouse Study

Representatives from compounds of formula I were tested for their effect on utriculi reduction on rhino mouse and directly compared to all-trans retinoic acid.

Rhino mouse utriculi reduction assay

Six to nine week old female hairless rhino mice (hr$^{rh}$/hr$^{rh}$) were produced in the Bristol-Myers Squibb colony. Test retinoids in ethanol vehicle (50 μl) were applied to the dorsal area (approximately 1.5×3 cm$^2$) of rhino mice once daily for 5 days (Monday to Friday). For various retinoids, a dose response was obtained with concentrations ranging from 0.00033 mM to 16.5 mM. The animals were sacrificed on the following Monday by CO$_2$ inhalation. A ⅞" full thickness punch was taken from the central dorsal area of each animal. The epidermis of the biopsy was removed from the dermis after incubation in 0.5% acetic acid overnight at 4° C. The separated epidermis was then fixed in formalin, dehydrated with ethanol, and cleared in xylene. To determine the utriculi diameter, each epidermis sheet was placed on a glass slide in xylene. For each specimen, the diameter of 40 utricules was measured with an image analysis system (IBM PC, Image Measure program and Olympus microscope with video camera). % Utriculi reduction was calculated as $$\left(1 - \frac{\text{utriculi diameter in the test group}}{\text{utriculi diammeter in the ethanol control group}}\right) \times 100\%$$

Since the maximum effect in this assay is approximately 60% utriculi reduction, the activity of various test compounds is reported as ED$_{30}$ in Table 1, the concentration to reach 30% (half-maximum) utriculi reduction.

TABLE 1

| Compound* | ED$_{30}$ (mM) |
|---|---|
| I$^2$e | 3.89 |
| I$^2$a | >10 |
| I$^2$g | 2.07 |

*Compounds I$^2$f and I$^2$d were also tested, but found to be inactive in this model.

The following biological test indicates that the compounds of the instant invention possess cytotoxicity activity normally associated with retinoids. Thus in one aspect, the invention provides a method of treating various tumors.

Cytotoxicity Result

The cytotoxicity assay was set up similar to those run by the National Cancer Institute (D. A. Scudiero, et al, "Evaluation of a Soluble Tetrazolium/Formazan Assay for Cell Growth and Drug Sensitivity in Culture Using Human and Other Tumor Cell Lines", *Cancer Research*, 48, 4827–4833, Sep. 1, 1988; M. C. Alley, et al, "Feasibility of Drug Screening with Panels of Human Tumor Cell Lines Using a Microculture Tetrazolium Assay", *Cancer Research*, 48, 589–601, Feb. 1, 1988) with the exception that the new vital stain alamarBLueTM was used to determine cellular viability. Briefly, the assayed involved plating 1000 cells per well in a volume of 120 μL in a 96 well flat-bottom dish (Corning) on day −1. Twenty-four hours later the appropriate dilution of a compound of formula I was added in a volume of 30 μL complete medium (final volume 150 μL). The plates were sealed with a plate sealer (Dynatech Labs) to prevent evaporation. On day 5 the mylar film was removed and 15 μL of sterile alamarblue was added to each well and the cells were incubated 37° C. 5% $CO_2$ for two hours. Using a Vmax plate reader the optical density for each well was determined having the $OD_{570}$ subtracted from the $OD_{600}$. The 100% signal was determined for cells grown in complete medium containing only 0.5% DMSO. All wells were set-up in triplicate and the mean values were plotted in FIG. 1. The $IC_{50}$ values were determined for the second experiment and are listed in table 2.

TABLE 2

$IC_{50}$ values for L2987 experiment 2

| Compound | $IC_{50}$ (uM) |
| --- | --- |
| All trans retinoic acid | 68 |
| I²a | 64 |
| I²b | 50 |

The compounds of formula I may be used topically or systemically, as anticancer agents and in the treatment, amelioration, or prevention of the skin disorders and rheumatic illnesses for which retinoic acid and other retinoids are useful. In this regard, they may be used for therapy in animals, including humans, of premalignant epithelial cell lesions, as a prophylaxis against tumor promotion in epithelial cells and treatment for dermatoses such as ichthyoses, follicular disorders, benign epithelial disorders, and other proliferative skin diseases (nonmalignant conditions of the skin that are characterized by epidermal cell proliferation or incomplete cell differentiation) such as acne, psoriasis, eczema, atopic dermatitis, nonspecific dermatitis and the like. The compounds of formula I may also be used in reversing and preventing the effects of irradiation damage to skin. When used for the above treatments they will usually be formulated with a pharmaceutically acceptable liquid, semi-solid, or solid carrier. A pharmaceutically acceptable carrier is a material that is nontoxic and generally inert and does not affect the functionality of the active ingredients adversely. Such materials are well known and include those materials sometimes referred to as diluents or vehicles (excipients) in the pharmaceutical formulation art. The carrier may be organic or inorganic in nature. Examples of pharmaceutically acceptable carriers that may be used to formulate a compound of formula I are water, gelatin, lactose, starch, mineral oil, cocoa butter, dextrose, sucrose, sorbitol, mannitol, gum acacia, alginates, cellulose, talc, magnesium stearate, polyoxyethylene sorbitan monolaurate, and other commonly used pharmaceutical carriers. In addition to a compound of formula I and carrier, the formulation may contain minor amounts of additives such as flavoring agents, coloring agents, thickening or gelling agents, emulsifiers, wetting agents, buffers, stabilizers, and preservatives such as antioxidants.

The dosages and dosage regimen in which the compounds of formula I are administered will vary according to the dosage form, mode of administration, the condition being treated and particulars of the patient being treated. Accordingly, optimal therapeutic concentrations will be best determined at the time and place through routine experimentation.

In the treatment of dermatoses, it will generally be preferred to administer the drug topically, though in certain cases such as treatment of severe cystic acne, oral administration may also be used. If the compounds according to the invention are used topically, it will be found that they exhibit a good activity over a very broad range of dilution; in particular, concentrations of the active compound or compounds ranging from 0.0005% to 2% by weight can generally be used. It is of course possible to use higher concentrations if this should become necessary for a particular application; however, the preferred concentration of active principle are from 0.002% to 1% by weight.

For topical administration the compounds of formula I are conveniently provided in the form of unguents, gels, creams, ointments, powders, dyeing compositions, solutions, suspensions, emulsions, lotions, sprays, adhesive plasters and impregnated pads. The compounds according to the invention can be mixed with inert nontoxic, generally liquid or pasty, bases suitable for topical treatment. Preparation of such topical formulations are well described in the art of pharmaceutical formulations as exemplified, for example, Remington's Pharmaceutical Science, Edition 17, Mack Publishing Company, Easton, Pa. Other medicaments can be added to such topical formulation for such secondary purposes as treating skin dryness, providing protection against light; other medications for treating dermatoses, preventing infection, reducing irritation, inflammation and the like.

The compounds according to the invention can also be used enterally. Orally, the compounds according to the invention are suitably administered at the rate of 2 μg to 2 mg per day per kg of body weight. The required dose can be administered in one or more portions. For oral administration, suitable forms are, for example, tablets, pills, dragees, syrups, suspensions, emulsions, solutions, powders and granules; a preferred method of administration consists in using pills containing from 0.1 mg to about 1 mg of active substance.

U.S. Pat. No. 4,876,381 issued on Oct. 24, 1989 to Lang et al. provides examples of formulations constituting gel, unguent, powder, cream, etc. for a retinoid compound. The aforesaid U.S. Patent can be used as a guide to formulate a compound of formula I and is herein incorporated by reference in its entirety.

Isotretinoin (Accutane®) and etretinate (Tegison®) are used clinically to treat severe recalcitrant cystic acne and severe recalcitrant psoriasis, including the erythrodermica and generalized pustular types, respectively. Their mode of use is amply illustrated in the Physician's Desk Reference, 47th Edition, 1993, published by Medical Economics Data. The compounds of formula I may also be used to treat severe recalcitrant cystic acne or severe recalcitrant psoriasis. In so doing, the compounds of the present invention may be used in a similar fashion to isotretinoin and etretinate; thus, the relevant sections on isotretinoin and etretinate in the Physician's Desk Reference will serve as a convenient guide which will obviate the need for any undue experimentation.

The compounds according to the invention can also be administered parenterally in the form of solutions or suspensions for intravenous or intramuscular perfusions or injections. In that case, the compounds according to the invention are generally administered at the rate of about 2 μg to 2 mg per day per kg of body weight; a preferred method of administration consists of using solutions or suspensions containing approximately from 0.01 mg to 1 mg of active substance per ml.

Several retinoids have been found to possess anti-tumor properties. Roberts, A. B. and Sporn, M. B. in "The Retinoids," Sporn, M. B., Roberts, A. B., and Goodman, D. S., eds, 1984, 2 pp. 209–286, Academic Press, New York; Lippman, S. M., Kessler, J. F., and Meyskens, F. L., *Cancer Treat. Rep.,* 1987, 71, p. 391; ibid., p. 493. As used herein, the term "anti-tumor" includes both chemopreventative (prophylactic or tumor promotion inhibiting) and therapeutic (curative) use. For example, all-trans retinoic acid can be used to treat acute promyelocytic leukemia. Huang, M. et al., Blood, 1988, 72, p. 567. Isotretinoin has been shown to be useful in prevention of second primary tumors in squamous-cell carcinoma of the head and neck. Hong, W. K. et al., *N. Engl. J. Med.,* 1990, 323, p. 795.

The compounds of formula I can also be used in substantially the similar manner to retinoids for treating (both chemopreventively and therapeutically) various tumors. For the compounds of this invention, the anti-tumor dose to be administered, whether a single dose, multiple dose, or a daily dose, will of course vary with the particular compound employed because of the varying potency of the compound, the chosen route of administration, the size of the recipient, the type of tumor, and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. An oncologist skilled in the art of cancer treatment will be able to ascertain, without undue experimentation, appropriate protocols for the effective administration of the compounds of this present invention, such as by referring to the earlier published studies on retinoids found to have anti-tumor properties. For example, for the prevention of second primary tumors with a compound of formula I in squamous-cell carcinoma of the head and neck, an oncologist may refer to the study by Hong, W. K. et al. in *N. Engl. J. Med.,* 1990, 323, p. 795. For treating acute promyelocytic leukemia, s/he may refer to the study by Huang, M. et al. in *Blood,* 1988, 72, p. 567.

What we claim is:

1. A compound of formula I

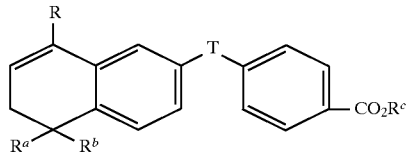

in which

T is —CONH— or —CH=CH—;

$R^a$ and $R^b$ are independently $C_{1-6}$ alkyl;

$R^c$ is $C_{1-6}$ alkyl or hydrogen; and

R is heteroaryl selected from pyrrolyl, pyrimidinyl, pyridinyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, indolyl, isoindolyl, quinolinyl, isoquinolinyl, benzothiazolyl, benzoxazolyl, benzimidazolyl, benzoxadiazolyl and benzofurazanyl, said heteroaryl radical being unsubstituted or substituted by one to three $C_{1-6}$ alkyl groups.

2. A compound of claim 1 wherein the heteroaryl group R is pyrimidinyl, pyridinyl, imidazolyl, pyridyl, pyrrolyl, thiazolyl, quinolinyl or isoquinolinyl, said heteroaryl group being unsubstituted or substituted by one to three $C_{1-6}$ alkyl groups.

3. A compound of claim 1 wherein R is of the formula

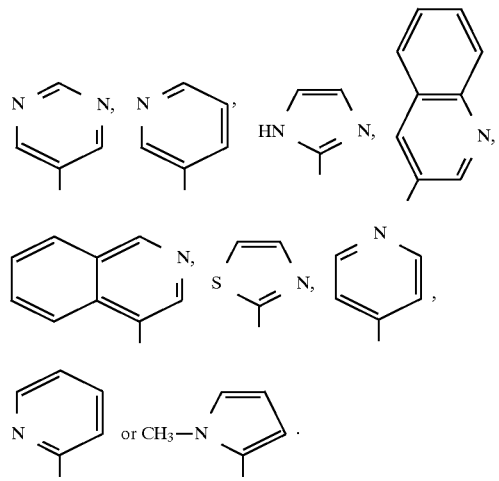

4. The compound of claim 1 that is 4-[[[[5,6-dihydro-5, 5-dimethyl-8-(5-pyrimidinyl)]-2-naphthalenyl]carbonyl] amino]benzoic acid.

5. The compound of claim 1 that is 4-[[[[5,6-dihydro-5, 5-dimethyl-8-(3-pyridinyl)]-2-naphthalenyl]carbonyl] amino]benzoic acid.

6. The compound of claim 1 that is 4-[[[[5,6-dihydro-5, 5-dimethyl-8-(2-N-methylpyrrolyl)]-2-naphthalenyl] carbonyl]amino]benzoic acid.

7. The compound of claim 1 that is 4-[[[[5,6-dihydro-5, 5-dimethyl-8-(4-pyridinyl)]-(2-naphthalenyl]carbonyl] amino]benzoic acid.

8. The compound of claim 1 that is 4-[[[[5,6-dihydro-5, 5-dimethyl-8-(2-imadazolyl)]-2-naphthalenyl]carbonyl] amino]benzoic acid.

9. The compound of claim 1 that is 4-[[[[5,6-dihydro-5, 5-dimethyl-8-(4-isoquinolinyl)]-2-naphthalenyl]carbonyl] amino]benzoic acid.

10. The compound of claim 1 that is 4-[[[[5,6-dihydro-5, 5-dimethyl-8-(3-quinolinyl)]-2-naphthalenyl]carbonyl] amino]benzoic acid.

11. The compound of claim 1 that is 4-[[[[5,6-dihydro-5, 5-dimethyl-8-(2-thiazolyl)]-2-naphthalenyl]carbonyl] amino]benzoic acid.

12. The compound of claim 1 that is 4-[[[[5,6-dihydro-5, 5-dimethyl-8-(2-pyridinyl)]-2-naphthalenyl]carbonyl] amino]benzoic acid.

13. The compound of claim 1 that is 4-[[(E)-5,6-dihydro-5-5-dimethyl-8-(3-pyridinyl) -2-naphthalenyl]ethenyl] benzoic acid.

* * * * *